(12) United States Patent
Lim

(10) Patent No.: US 10,835,334 B2
(45) Date of Patent: Nov. 17, 2020

(54) MASTER CONSOLE FOR SURGICAL ROBOT

(71) Applicant: meerecompany Inc., Hwaseong-si (KR)

(72) Inventor: Hyung Keun Lim, Yongin-si (KR)

(73) Assignee: meerecompany Inc., Hwaseong-si (KR)

( * ) Notice: Subject to any disclaimer, the term of this patent is extended or adjusted under 35 U.S.C. 154(b) by 69 days.

(21) Appl. No.: 16/109,378

(22) Filed: Aug. 22, 2018

(65) Prior Publication Data

US 2019/0239971 A1  Aug. 8, 2019

(30) Foreign Application Priority Data

Feb. 5, 2018 (KR) ........................ 10-2018-0014174
Feb. 5, 2018 (KR) ........................ 10-2018-0014175

(51) Int. Cl.
*A61B 34/37* (2016.01)
*B25J 13/04* (2006.01)
*G05G 1/38* (2008.04)

(52) U.S. Cl.
CPC ............... *A61B 34/37* (2016.02); *B25J 13/04* (2013.01); *G05G 1/38* (2013.01); *A61B 2560/0462* (2013.01); *A61B 2560/0487* (2013.01)

(58) Field of Classification Search
CPC ................................... B25J 13/04; G05G 1/38
See application file for complete search history.

(56) References Cited

U.S. PATENT DOCUMENTS

| 8,423,182 B2* | 4/2013 | Robinson ............... A61B 34/25 700/245 |
| 2007/0152508 A1* | 7/2007 | Mezhinsky ......... A61F 9/00736 307/119 |
| 2011/0106068 A1* | 5/2011 | Horvath ................. A61B 17/00 606/11 |
| 2017/0000575 A1* | 1/2017 | Griffiths ................. A61B 34/25 |
| 2019/0239971 A1* | 8/2019 | Lim ....................... A61B 34/37 |

FOREIGN PATENT DOCUMENTS

| JP | 2013-101080 A | 5/2013 |
| JP | 2015-213753 A | 12/2015 |
| JP | 2017-515522 A | 6/2017 |
| KR | 10-2015-0094134 A | 8/2015 |
| KR | 10-2016-0105923 A | 9/2016 |
| KR | 10-2017-0040391 A | 4/2017 |

* cited by examiner

*Primary Examiner* — Vicky A Johnson
(74) *Attorney, Agent, or Firm* — Novick, Kim & Lee, PLLC; Sang Ho Lee

(57) ABSTRACT

Provided is a master console for a surgical robot. The master console includes: a base unit including a first base and a second base, the first and second bases being provided parallel to each other; and a foot pedal unit between the first base and the second base, wherein the foot pedal unit includes at least one foot pedal switch capable of being manipulated by a foot of an operator, a foot panel configured to support the at least one foot pedal switch, and a footrest extending outward from the foot panel.

19 Claims, 23 Drawing Sheets

MASTER CONSOLE FOR SURGICAL ROBOT

CROSS-REFERENCE TO RELATED APPLICATIONS

This application claims the benefit of Korean Patent Application Nos. 10-2018-0014174 and 10-2018-0014175, filed on Feb. 5, 2018, in the Korean Intellectual Property Office, the disclosures of which are incorporated herein in their entirety by reference.

BACKGROUND

1. Field

One or more embodiments relate to a master console for a surgical robot, and more particularly, to a master console for a surgical robot in which convenience and manipulative accuracy of an operator (a doctor who performs an operation) are enhanced.

2. Description of the Related Art

Surgical robots refer to robots having a function capable of replacing a surgical act performed by a surgeon. These surgical robots can operate more accurately and precisely than humans and perform remote operations.

Currently, there are surgical robots being developed worldwide, such as bone surgery robots, laparoscopic surgery robots, stereotactic surgery robots, and the like.

A conventional surgical robot generally has a master console and a slave robot. When an operator manipulates an operating lever (e.g., a handle) included in the master console, a surgical tool coupled to a robot arm of the slave robot is manipulated, thereby performing an operation.

When an operation is performed using a surgical robot, an operator takes a short break from a master console, to relieve fatigue that has been accumulated for a long time period or while a surgical tool is replaced. Meanwhile, foot pedals are located below a master console, and thus in order for an operator to take a break safely and comfortably without touching the foot pedals during the break, an instrument for resting feet is needed. An existing operator has to take a break by simply mounting his or her feet on a base or outside a master console. However, when the operator's feet are mounted on a base, a foot pedal may be touched by mistake, and thus there is a risk of surgical accidents, and when an operator takes a break away from a master console, inconveniences and problems exist, e.g., resetting to perform an operation again.

In addition, as described above, foot pedals with various functions are located below a master console, and an operator steps on a foot pedal according to a surgical circumstance, thereby manipulating a surgical instrument. On the other hand, in an actual surgical situation, an operator is required to concentrate on the surgical situation visually through a display installed at an upper end of the master console, and thus there is a risk of manipulating a wrong foot pedal by mistake.

The foregoing related art is technical information that has been retained by an inventor of the present disclosure to achieve the present disclosure, or has been acquired in a process of achieving the present disclosure, and is not necessarily a known technology disclosed to the general public prior to the filing of the present disclosure.

SUMMARY

One or more embodiments include a master console for a surgical robot in which convenience and manipulative accuracy of an operator are enhanced.

Additional aspects will be set forth in part in the description which follows and, in part, will be apparent from the description, or may be learned by practice of the presented embodiments.

According to one or more embodiments, a master console for a surgical robot includes: a base unit including a first base and a second base, the first and second bases being provided parallel to each other; and a foot pedal unit arranged between the first base and the second base, wherein the foot pedal unit includes: at least one foot pedal switch capable of being manipulated by a foot of an operator; a foot panel configured to support the at least one foot pedal switch; and a footrest extending outward from the foot panel.

In addition, the foot pedal unit may move along the first base and the second base according to body information of the operator.

In addition, the footrest may extend such that the footrest surrounds the base unit.

In addition, the footrest may be inclined with respect to an upper surface of the base unit.

In addition, the foot pedal unit may further include a sub-footrest protruding from an upper surface of the foot panel and located between the first base and the second base.

In addition, the sub-footrest may include an inclined surface inclined with respect to a ground, and a recognition protrusion protruding from the inclined surface.

In addition, the foot pedal unit may further include: at least one first switch provided on a surface of the foot panel, wherein a first pattern is on an outer surface of the at least one first switch; and at least one second switch provided on a surface of the foot panel at a height different from that of the at least one first switch, wherein a second pattern is on an outer surface of the at least one second switch, the second pattern being different from the first pattern.

In addition, an amount by which at least one of the first pattern and the second pattern protrudes may gradually increase in a direction.

In addition, the foot pedal unit may further include: a first sensor configured to sense a position of a foot of the operator in a leftward or rightward direction; and a second sensor configured to sense a position of a foot of the operator in a forward or backward direction.

In addition, the at least one first switch may be inclined with respect to the foot panel, and the at least one second switch may be parallel to the foot panel.

In addition, a rotational shaft may be provided in a front end portion of the at least one first switch such that the at least one first switch is operable by a foot of the operator pressing a rear end portion of the at least one first switch, and a rotational shaft may be provided in a rear end portion of the at least one second switch such that the at least one second switch is operable by a foot of the operator pressing a front end portion of the at least one second switch.

In addition, the at least one first switch may be configured such that an amount by which the first pattern protrudes increases towards a rear end portion of the at least one first switch, and the at least one second switch may be configured such that an amount by which the second pattern protrudes increases towards a front end portion of the at least one second switch.

In addition, the at least one foot pedal switch may include: a pair of first switches disposed on a surface of the foot panel, and each having a first protrusion protruding from a side of each of the pair of first switches, the sides having the first protrusions being disposed opposite to each other; and a pair of second switches disposed on another surface of the foot panel at a height different from that of the pair of first switches, and each having a second protrusion protruding from a side of each of the pair of second switches, the side having the second protrusions being disposed opposite to each other.

In addition, the foot panel may include a first surface and a second surface, the first surface having a first slope with respect to a ground and the second surface having a second slope different from that of the first surface, and may be located between the first base and the second base, and the at least one foot pedal switch may include: at least one first switch including a first touch sensor provided on the first surface; and at least one second switch including a second touch sensor provided on the second surface.

In addition, a pattern may be formed on an outer surface of each of the first touch sensor and the second touch sensor, the patterns being different from each other.

Further, the foot pedal can include a first step and a second step, wherein the at least one first switch includes a first pedal switch and a second pedal switch disposed on the first step, and wherein the at least one second switch includes a third pedal switch and a fourth pedal switch disposed on the second step.

Further, in the master console, a height of the second pattern of the third pedal switch gradually increases in a direction and a height of the second pattern of the fourth pedal switch gradually increases in another direction opposite to the direction of the pattern of the third pedal switch.

Further, in the master console, the at least one first switch further includes a fifth pedal switch disposed on the first step and the at least one second switch further includes a sixth pedal switch disposed on the second step, and the foot pedal further includes a sub-footrest located on the first and second steps and between the first pedal switch and the fifth pedal switch, such that the sub-footrest is configured to distinguish locations of the first to fourth pedal switches from those of the fifth and sixth pedal switches.

Further, in the master console, the foot pedal can include a sub-footrest located on the first and second steps and between the first pedal switch and the second pedal switch, such that the sub-footrest is configured to distinguish locations of the first and third pedal switches from those of the second and fourth pedal switches.

Further, in the mater console, the foot pedal further includes a seventh pedal switch disposed on a side surface thereof.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
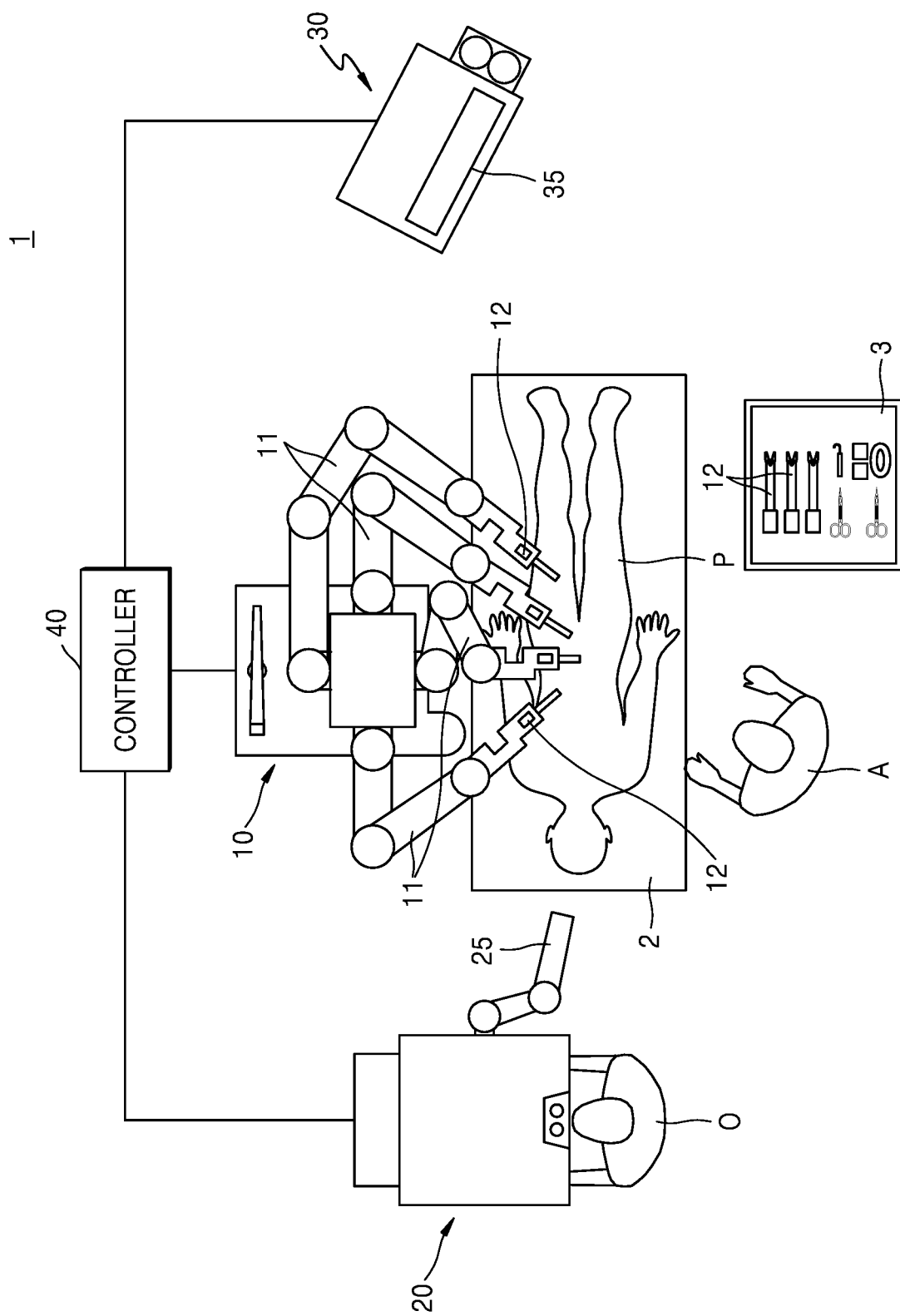
FIG. 1 is a plan view illustrating an overall structure of a surgical robot according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, embodiments of the present disclosure will be described in detail with reference to the accompanying drawings in such a way that the disclosure may be carried out by one of ordinary skill in the art to which the present disclosure pertains without undue difficulty. The present disclosure may be embodied in many different forms and is not limited by the embodiments set forth herein.

FIG. 1 is a plan view illustrating an overall structure of a surgical robot 1 according to an embodiment.

Referring to FIG. 1, the surgical robot 1 includes a slave robot 10 configured to perform surgery on a patient P lying on an operating table 2, and a master console 20 allowing an operator O to remotely control the slave robot 10. In addition, the surgical robot 1 may include a vision cart 30. Through a display unit 35 of the vision cart 30, an assistant A may check the progress of surgery.

The slave robot 10 may include at least one robot arm 11. Generally, robot arms have a function similar to that of human arms and/or wrists and include a device capable of attaching a predetermined tool to a wrist part. In the present specification, each robot arm 11 may be defined as a device including components such as an upper arm, a lower arm, a wrist, an elbow, and the like, and surgical instruments coupled to the wrist, and the like. Each robot arm 11 of the slave robot 10 may be configured to be driven with redundant degrees of freedom. Each robot arm 11 may include, for example, a surgical instrument insertable into a surgical site of the patient P, a yawing drive unit configured to rotate the surgical instrument in a yaw direction according to a surgical position, a pitch drive unit configured to rotate the surgical instrument in a pitch direction perpendicular to rotational driving of the yawing drive unit, a transfer drive unit configured to transfer the surgical instrument in a longitudinal direction, a rotational drive unit configured to rotate the surgical instrument, and a surgical instrument end effector installed at an end portion of the surgical instrument and configured to incise or cut a surgical lesion. However, the configurations of each robot arm 11 are not limited to the above examples, and these illustrations should be understood as not limiting the scope of the present disclosure. Here, a detailed description of actual control processes, such as rotation, movement, and the like of each robot arm 11 in a corresponding direction as the operator O manipulates an operating lever will be omitted herein.

At least one slave robot 10 may be used to perform surgery on the patient P, and each slave robot 10 may be independently configured. In addition, as described above, embodiments of the present disclosure may be widely applied to surgeries in which a variety of surgical endoscopes in addition to laparoscopes (e.g., a thoracoscope, an arthroscope, a rhinoscope, and the like) are used.

The master console 20 and the slave robot 10 are not necessarily separated from each other as physically independent separate devices, and may be provided in an integrated form. However, hereinafter, a case in which the master console 20 and the slave robot 10 are physically separated from each other will be mainly described for convenience of explanation.

Figure 2:
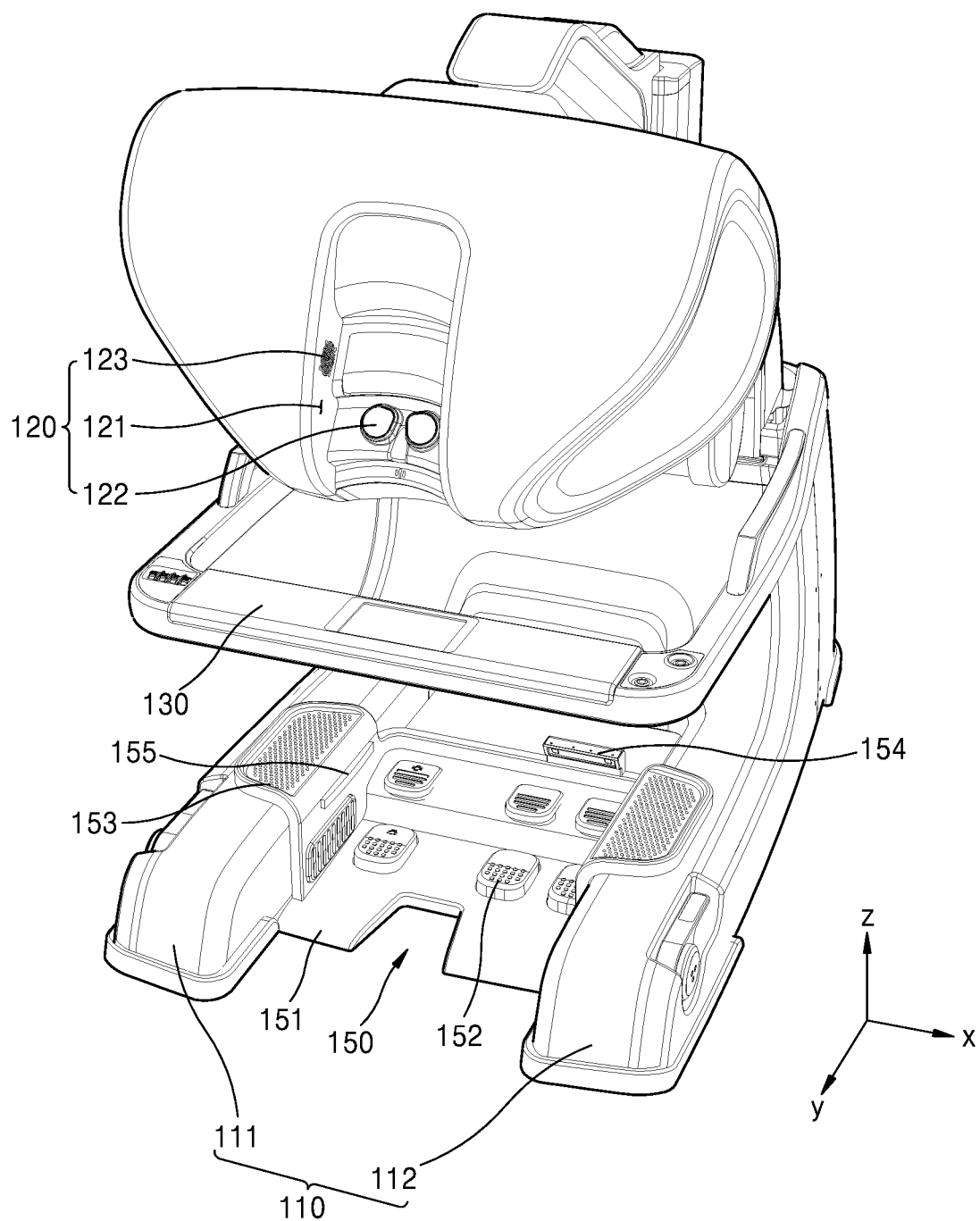
FIG. 2 is a perspective view illustrating a master console for a surgical robot, according to an embodiment.

The master console 20 includes an operating lever (not shown) and a display member 122 (see FIG. 2). In addition, the master console 20 may further include an external display device 25 capable of displaying a state of the operator O on an outer side thereof.

In detail, the master console 20 includes operating levers (not shown) configured to be grabbed and manipulated with both hands of the operator O. The operating levers may be configured as two or more handles, and a manipulation signal according to handle manipulation of the operator O is transmitted to the slave robot 10 via a wired or wireless communication network, and the at least one robot arm 11 is controlled by the manipulation signal. That is, surgical operations such as position movement, rotation, a cutting operation, and the like may be performed by the handle manipulation of the operator O.

For example, the operator O may manipulate the at least one robot arm 11, a surgical instrument 12, or the like by using handle-type operating levers. These operating levers may have various mechanical configurations according to an operation mode thereof, and may include a master handle configured to manipulate an operation of the at least one robot arm 11, the surgical instrument 12, or the like, and various forms configured to operate the at least one robot arm 11 of the slave robot 10 and/or other surgical equipment, such as various input tools added to the master console 20 to manipulate a function of an entire system, e.g., a joystick, a keypad, a trackball, and a touch screen. Here, the shape of operating levers is not limited to a handle shape, and is not particularly limited as long as it allows the operation of the at least one robot arm 11 to be controllable via a network such as a wired or wireless communication network.

An image of a surgical site, which is captured by an endoscope, is displayed on the display member 122 (see FIG. 2) of the master console 20. In addition, a predetermined virtual operation board may be displayed on the display member 122 along with the image captured by an endoscope or may be displayed independently.

The display member 122 may be provided in various forms that allow the operator O to identify an image. For example, a display device may be installed so as to correspond to both eyes of the operator O. In some embodiments, as the display device, one or more monitors may be provided, and pieces of information needed for surgery may be separately displayed on each monitor. The number of display members 122 may be variously determined according to the kind, type, or the like of information required to be displayed. A detailed description of the master console 20 is provided below.

The vision cart 30 may be installed separately from the slave robot 10 or the master console 20, and the progress of surgery may be checked outside via the display unit 35. An image displayed on the display unit 35 may be the same as that displayed on the display member 122 of the operator O. The assistant A may assist a surgical operation of the operator O while checking the image on the display unit 35. For example, the assistant A may select, from an instrument cart 3, the surgical instrument 12 needed according to the progress of surgery, and may replace the surgical instrument 12.

A controller 40 may be connected to the slave robot 10, the master console 20, and the vision cart 30 to transmit or receive respective signals thereto or therefrom. A detailed description of the controller 40 is provided below.

FIG. 2 is a perspective view illustrating a master console 100 for a surgical robot, according to an embodiment.

Referring to FIG. 2, the master console 100 may include a base unit 110, a head unit 120, a manipulation unit 130, and a foot pedal unit 150.

The base unit 110 forms an external appearance of the master console 100, and is configured to support the master console 100 on the ground. The base unit 110 extends from the ground towards the head unit 120. The base unit 110 may include, at a lower end thereof, a first base 111 and a second base 112 that are provided parallel to each other.

The head unit 120 may be located at an upper side of the master console 100, and may include an insert groove 121 into which a head of the operator O can be inserted, the display member 122 configured to provide the operator O with a surgical image, a fan (not shown) or a head recognition sensor 123 configured to sense a position of the head of the operator O, and a speaker (not shown) configured to transmit a voice signal to the operator O.

The manipulation unit 130 may allow the operator O to manipulate the slave robot 10 using handle-type operating levers (not shown). On a side of the manipulation unit 130, a touchscreen-type input device may be provided to allow the operator O to manipulate input instructions.

Figure 3:
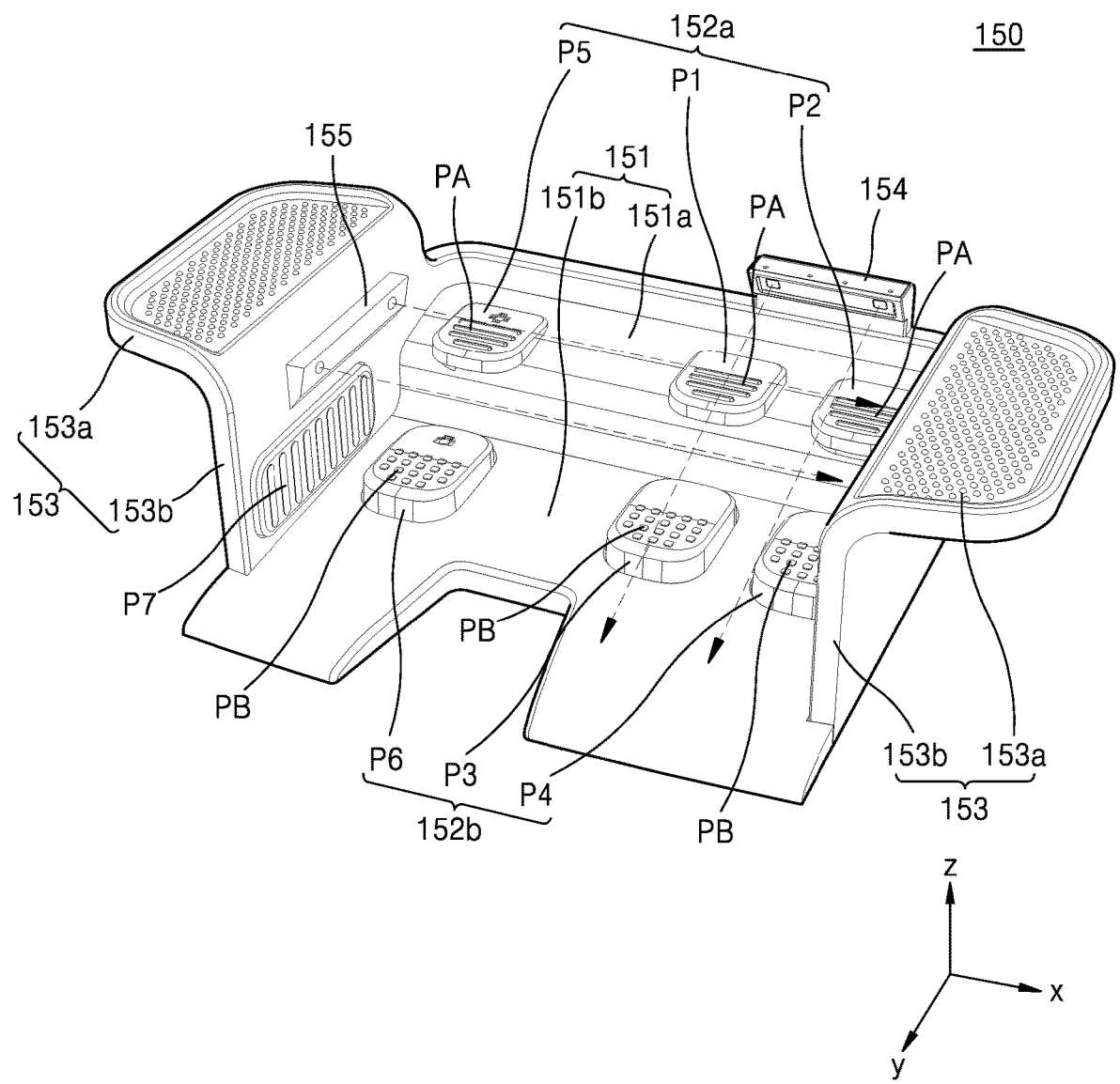
FIG. 3 is a perspective view illustrating a foot pedal unit of FIG. 2.
Figure 4A:
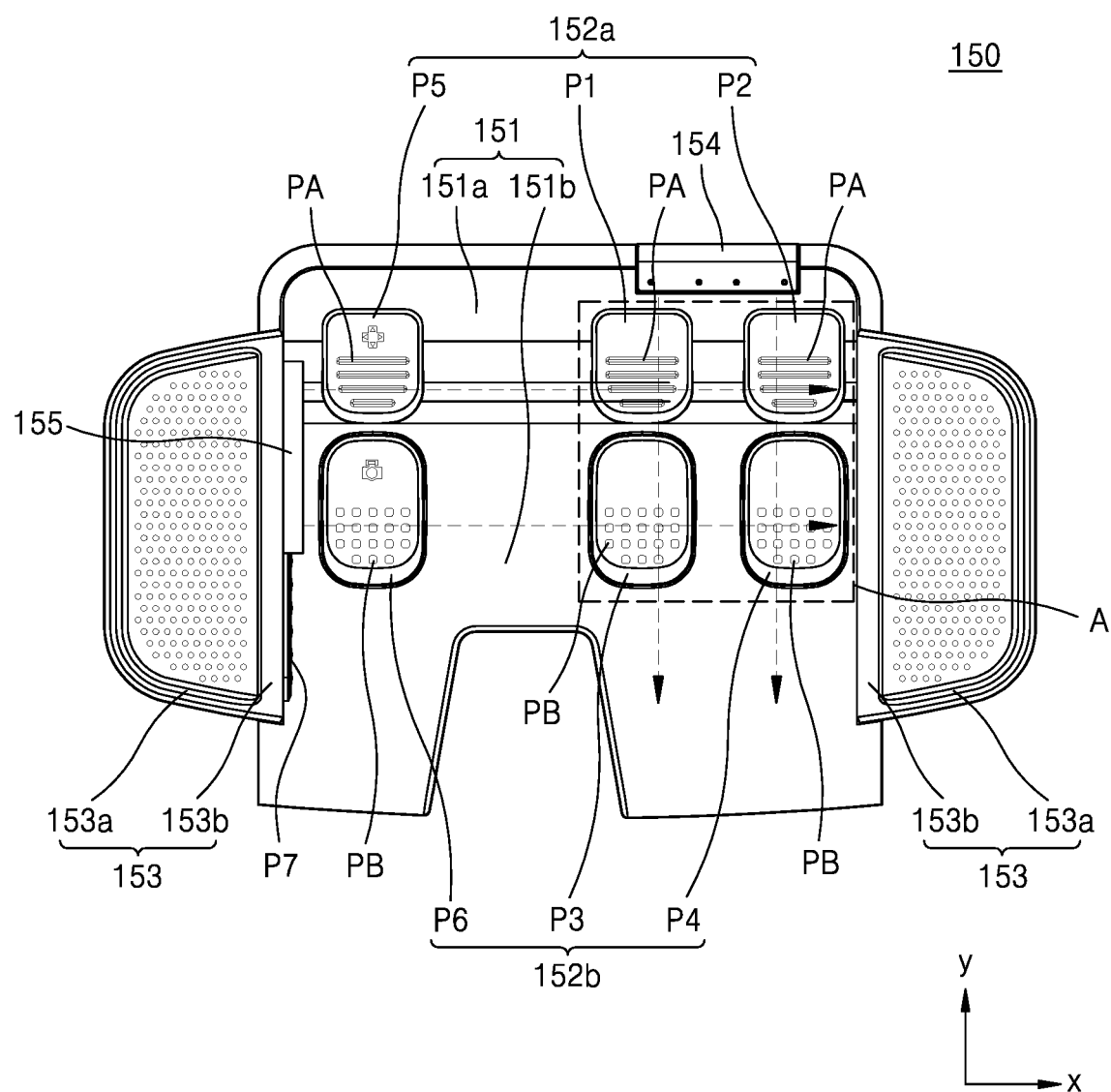
FIG. 4A is a plan view illustrating the foot pedal unit of FIG. 3.
Figure 4B:
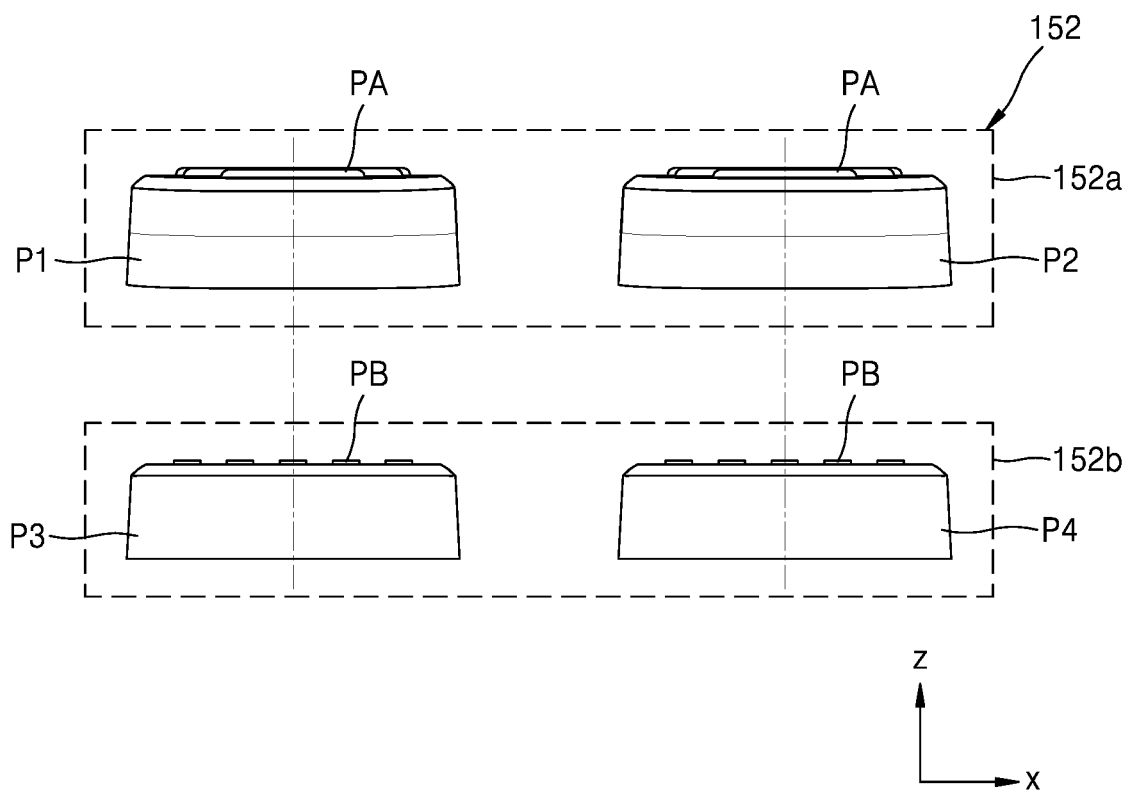
FIG. 4B is an enlarged front view of region A of FIG. 4A.

FIG. 3 is a perspective view of the foot pedal unit 150 of FIG. 2. FIG. 4A is a plan view of the foot pedal unit 150 of FIG. 3. FIG. 4B is an enlarged front view of region A of FIG. 4A.

Hereinafter, a forward or front end direction is defined as a direction toward the operator O who is seated, and a backward or rear end direction is defined as a direction away from the operator O who is seated.

Referring to FIGS. 2 to 4B, the foot pedal unit 150 may be located below the manipulation unit 130, and may be installed between the first base 111 and the second base 112. A foot of the operator O may cause the foot pedal unit 150 to generate an input signal. The foot pedal unit 150 may include a foot panel 151, a foot pedal switch 152, footrests 153, a first sensor 154, and a second sensor 155.

The foot panel 151 may be installed between the first base 111 and the second base 112, and may be provided in a stepped form in a forward or backward direction. The foot panel 151 may include a first step 151a provided at an upper end thereof and a second step 151b provided at a lower end thereof. The foot panel 151 may linearly move along the first base 111 and the second base 112. For example, the controller 40 drives a first drive unit 41, according to body information of the operator O, to move the foot panel 151 linearly (forward or backward), and accordingly, the operator O may perform surgery at an optimal position for manipulation of the foot pedal unit 150.

The foot pedal switch 152 is operated by a foot of the operator O positioned in the master console 100, and at least one foot pedal switch 152 may be provided on a surface of the foot panel 151. The foot pedal switch 152 may include a plurality of first switches 152a provided on the first step 151a and a plurality of second switches 152b provided on the second step 151b.

The first switches 152a and the second switches 152b have different patterns formed on respective surfaces thereof such that the position and function of each pedal switch may be recognized by the feeling on a foot of the operator O. Each of the first switches 152a may have a first pattern PA on an outer surface thereof, and each of the second switches 152b may have, on an outer surface thereof, a second pattern PB different from the first pattern PA. The operator O may distinguish the first pattern PA from the second pattern PB by the feeling on a foot, and thus may distinguish the first switches 152a from the second switches 152b while keeping an eye on the display member 122 of the head unit 120 during surgery.

The first pattern PA and the second pattern PB have different shapes so that the operator O can distinguish positions of the first step 151a and the second step 151b from each other. However, the first pattern PA and the second pattern PB are not limited to particular shapes illustrated in the drawings, and may have various shapes such as an embossed form and/or a sunken form.

The first pattern PA and the second pattern PB may be provided at positions to which a force may be applied by a foot of the operator O. The first pattern PA can be provided on an end portion of the first switch 152a to which a force may be applied by a foot of the operator O, and the second pattern PB can be provided on an end portion of the second switch 152b to which a force may be applied by a foot of the operator O. Since the first pattern PA and the second pattern PB are provided on regions to which a force may be directly applied by the operator O, the operator O may recognize patterns easily and rapidly.

The first switch 152a may include a first pedal switch P1 and a second pedal switch P2 that are provided adjacent to each other on a side of the first step 151a. For example, the first pedal switch P1 may be used to implement a function such as cutting using the surgical instrument 12 in a bipolar manner, or setting, changing a position, or the like of the surgical instrument 12. The second pedal switch P2 may be used to perform a cutting operation using the surgical instrument 12 in a monopolar manner. The first switch 152a may include a fifth pedal switch P5 located on another side of the first step 151a. The fifth pedal switch P5 may be used to implement a clutch mode of the surgical instrument 12.

The second switch 152b may include a third pedal switch P3 and a fourth pedal switch P4 that are provided adjacent to each other on a side of the second step 151b. For example, the third pedal switch P3 may be used to implement a cauterization function using the surgical instrument 12 in a bipolar manner. The fourth pedal switch P4 may be used to implement a cauterization function using the surgical instrument 12 in a monopolar manner. The second switch 152b may include a sixth pedal switch P6 disposed on another side of the second step 151b. The sixth pedal switch P6 may be used to manipulate a surgical instrument to perform a function of an endoscope. Specifically, when the sixth pedal switch P6 is activated, the position of the at least one robot arm 11 is fixed, and functions such as focusing, zooming, movement, and the like of a camera may be performed.

The foot pedal switch 152 may also be provided at a side surface of the foot panel 151. For example, a seventh pedal switch P7 may be provided at a side surface of the foot pedal unit 150 such that activation and non-activation of the at least one robot arm 11 may be controlled. The foregoing description of the functions of the first to seventh switches P1 to P7 is provided for illustrative purposes, and the first to seventh switches P1 to P7 may perform various functions without being limited to those in the foregoing description.

The first pattern PA of each of the first switches 152a may have the same form. As illustrated in FIG. 4A, the first pedal switch P1, the second pedal switch P2, and the fifth pedal switch P5 have the first pattern PA in the same form. In addition, the second pattern PB of each of the second switches 152b may have the same form. The third pedal switch P3, the fourth pedal switch P4, and the sixth pedal switch P6 each have the second pattern PB in the same form.

The footrests 153 may extend outward from the foot panel 151. The footrests 153 may be connected such that they respectively surround the first base 111 and the second base 112. The footrests 153 may include a first footrest configured to surround the first base 111 and a second footrest configured to surround the second base 112.

The footrests 153 may include foot plates 153a located on upper surfaces of the first base 111 and the second base 112, and connecting walls 153b extending along inner walls of the first base 111 and the second base 112 and connected to the respective foot plates 153a. The footrests 153 extend upward from the first base 111 and the second base 112, and thus may be provided at a height greater than that of the foot panel 151.

The foot plates 153a are provided with a plurality of protrusions on an upper surface thereof, and thus the operator O may easily recognize positions of the footrests 153. When an operation is performed in a state in which a face of the operator O is positioned in the head unit 120, it is necessary that a foot of the operator O is removed from a foot pedal switch for safety reasons. In this case, the operator O cannot visually identify the positions of the footrests 153, but may sense the positions of the footrests 153 using the feel of the protrusions. In addition, although not shown in the drawings, in another embodiment, the foot plates 153a may have vent holes such that air can be discharged to the feet of the operator O.

The footrests 153 may allow the operator O to rest his or her feet thereon when a surgical operation is temporarily stopped or stopped for a break taken by the operator O or replacement of a surgical instrument. Since the operator O can comfortably rest his or her feet on the footrests 153, fatigue due to the surgical operation may be reduced. The footrests 153 are formed integrally with the foot panel 151, and thus the operator O may take a break at an optimal position according to body information.

The first sensor 154 and the second sensor 155 may be provided in the foot pedal unit 150 such that the position of the foot of the operator O can be sensed. The first sensor 154 may sense, in a first direction (y axis), whether the foot of the operator O is located on the left or right side of the first switches 152a and/or the second switches 152b. When laser beams, infrared rays, or the like are emitted in the first direction, the first sensor 154 may sense whether the foot of the operator O is located on the left or right side. The second sensor 155 may sense, in a second direction (x axis), whether the foot of the operator O is located on the first step 151a and/or the second step 151b. When laser beams, infrared rays, or the like are emitted in the second direction, the second sensor 155 may sense whether the foot of the operator O is located in a forward or backward direction.

Figure 4C:
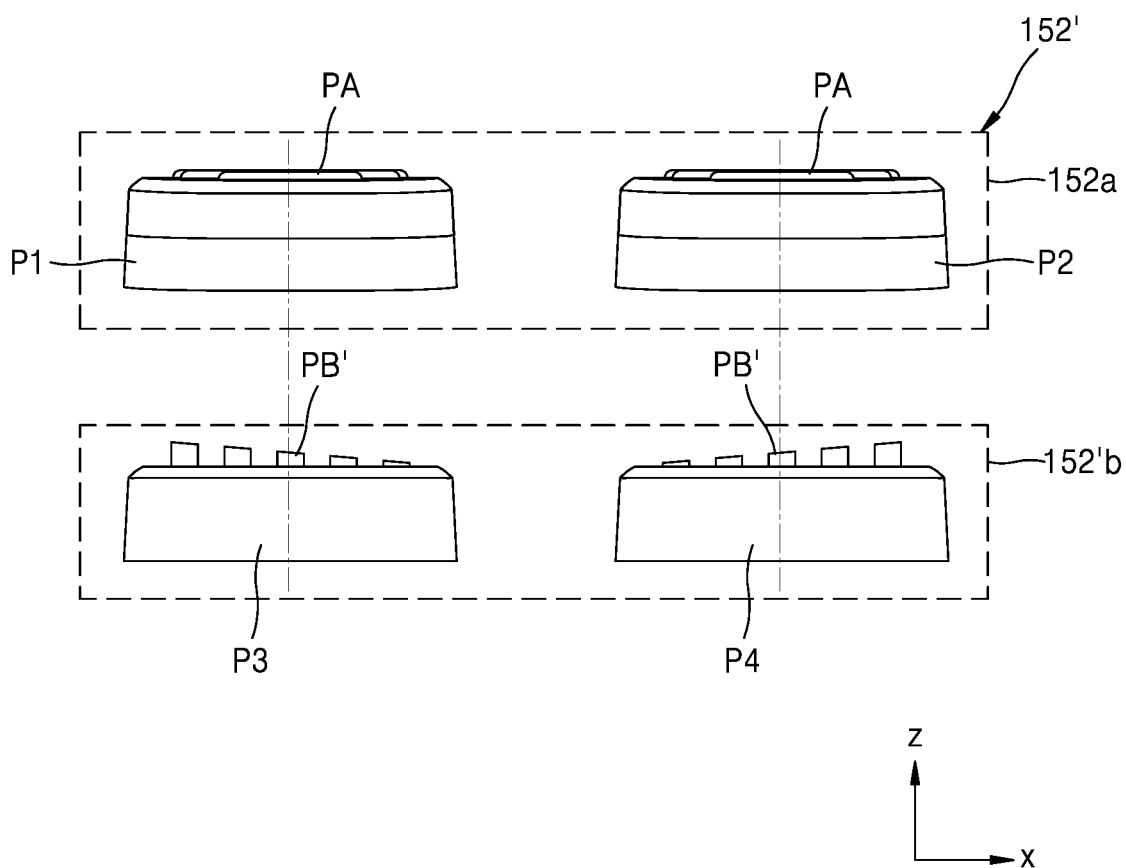
FIG. 4C is a front view illustrating a modified example of foot pedal switches of FIG. 3.

FIG. 4C is a front view illustrating a foot pedal switch 152', which is a modified example of the foot pedal switch 152 of FIG. 3.

Referring to FIG. 4C, the foot pedal switch 152' may be configured such that the amount by which second patterns PB' protrude increases in a direction. The amount by which the second patterns PB' protrude may gradually increase toward outer sides of the third pedal switch P3 and the fourth pedal switch P4. The operator O may identify the third pedal switch P3 or the fourth pedal switch P4 by sensing a protrusion direction of the second patterns PB'.

Although not shown in the drawings, the amount by which the second patterns PB' protrude may gradually increase toward inner sides of the third pedal switch P3 and the fourth pedal switch P4. In addition, the amount by which the first patterns PA protrude may also gradually increase toward inner or outer sides of the first pedal switch P1 and the second pedal switch P2.

Figure 5:
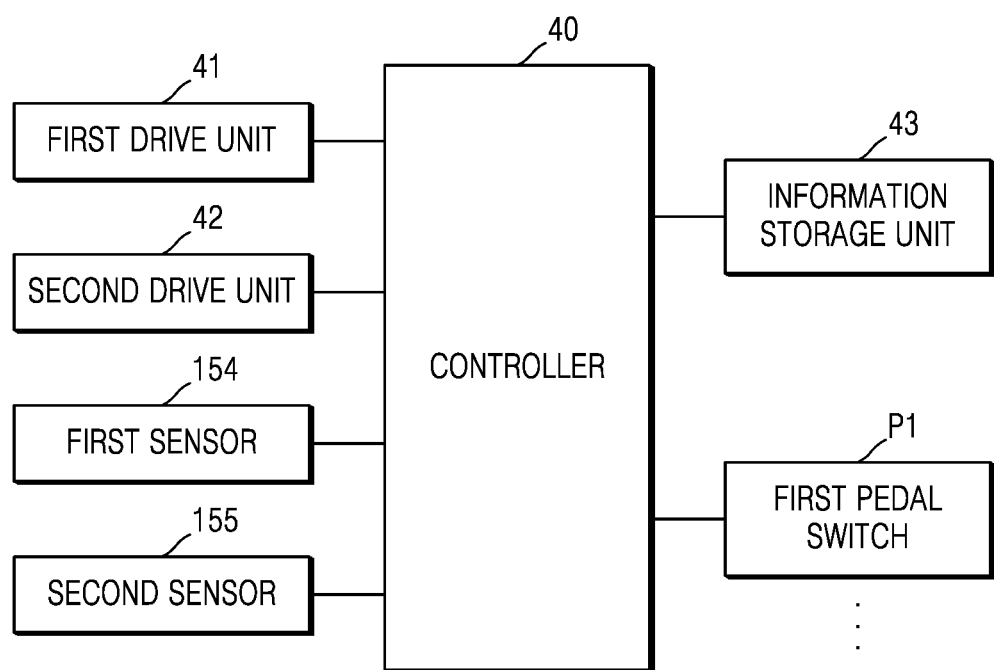
FIG. 5 is a configurational diagram illustrating partial configurations of the foot pedal unit of FIG. 2.

FIG. 5 is a configurational diagram illustrating partial configurations of the foot pedal unit 150 of FIG. 2.

Referring to FIG. 5, the controller 40 may be connected to each of a plurality of drive units to generate a driving signal to set the position of the foot pedal unit 150. In addition, the controller 40 may be connected to each pedal switch and receive an operation signal from the corresponding pedal switch, thereby driving the slave robot 10.

The controller 40 may be connected to an information storage unit 43 to move the position of the foot pedal unit 150 according to body information of the operator O. For example, when the operator O who is seated on the master console 100 loads body information from the information storage unit 43, the controller 40 may control the first drive unit 41 to move the position of the foot pedal unit 150.

The controller 40 may be connected to the first sensor 154 and the second sensor 155 to identify the position of the foot of the operator O. The first sensor 154 and the second sensor 155 may sense where a foot of the operator O is located among the first to fourth pedal switches P1 to P4.

The master console 100 for a surgical robot, according to an embodiment, may reduce fatigue of the operator O. Since the footrests 153 are provided on a side of the foot pedal unit 150, the operator O may easily and comfortably rest his or her feet on the footrests 153 when a surgical operation is temporarily stopped.

In particular, since the footrests 153 are separated from the foot pedal switch 152, operation of the foot pedal switch 152 due to carelessness of the operator O when the surgical operation is stopped may be prevented. In addition, the footrests 153 extend along the base unit 110, and thus an additional space is not required for installation of the footrests 153, and the footrests 153 may be compactly installed using an existing base unit.

When complicated and diverse surgeries are simultaneously performed or the function of the surgical instrument 12 is changed due to replacement of the surgical instrument 12, the operator O has to change the foot pedal switch 152. In one embodiment, when the operator O has to cauterize another surgical site after incising any one surgical site of a patient, the operator O has to change a manipulation target from the first switches 152a to the second switches 152b. In another embodiment, when a bipolar-type surgical instrument is replaced with a monopolar-type surgical instrument after being used, the operator O has to change a manipulation target from the first or third pedal switch P1 or P3 on the left side to the second or fourth pedal switch P2 or P4.

However, to continuously perform surgery, the operator O has to maintain a state in which the head of the operator O is inserted into the head unit 120, and thus the operator O cannot identify the position of each switch of the foot pedal switch 152. If the operator O removes his or her face from the head unit 120 to check the position of the foot pedal switch 152, an inconvenience such as a resetting operation needs to be performed in order to progress an operation.

In the master console 100 for a surgical robot, according to an embodiment, since the first switches 152a and the second switches 152b of the foot pedal unit 150 have different patterns, the position of the foot pedal switch 152 may be recognized without being visually identified by the operator O. That is, the operator O may distinguish a pedal switch on the first step 151a from a pedal switch on the second step 151b by the feeling on the feet. In addition, the operator O may distinguish pedal switches on the left and right sides of the foot pedal switch 152' from each other by recognizing a direction in which the first pattern PA or the second pattern PB protrudes.

In the master console 100 for a surgical robot, according to an embodiment, since the operator O can accurately recognize the position of the foot pedal switch 152, a malfunction may be prevented.

Figure 6:
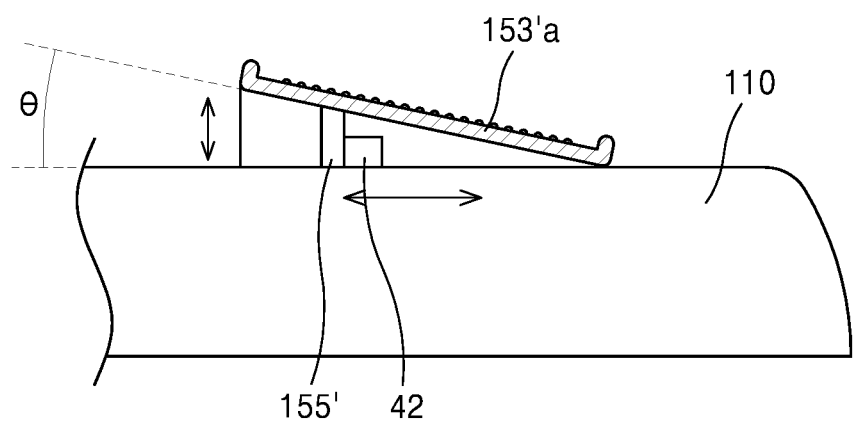
FIG. 6 is a schematic cross-sectional view of a foot pedal unit according to another embodiment.

FIG. 6 is a schematic cross-sectional view of a foot pedal unit according to another embodiment.

Referring to FIGS. 5 and 6, the foot pedal unit may have foot plates 153'a configured to be inclined with respect to the base unit 110. A second drive unit 42 may drive a vertical movement unit 155' such that the foot plates 153'a are inclined with respect to an upper surface of the base unit 110.

Inclination angles (θ) of the foot plates 153'a may be directly controlled by the operator O or may be set using the stored body information of the operator O. For example, the controller 40 may control the second drive unit 42 to be driven according to body information stored in the information storage unit 43, thereby adjusting the inclination angles (θ) of the foot plates 153'a.

Figure 7:
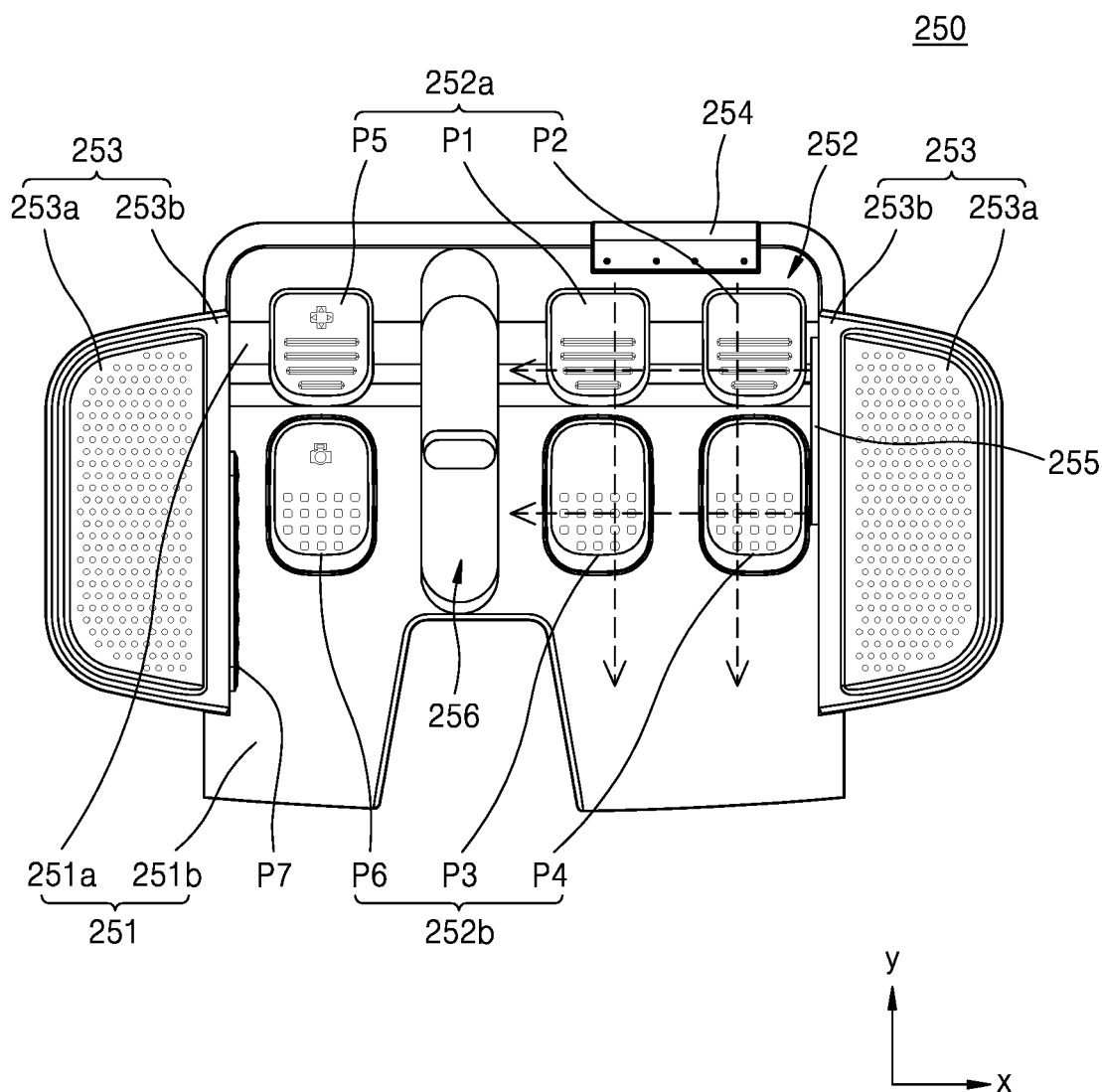
FIGS. 7 and 8 are views illustrating foot pedal units according to other embodiments.
Figure 8:
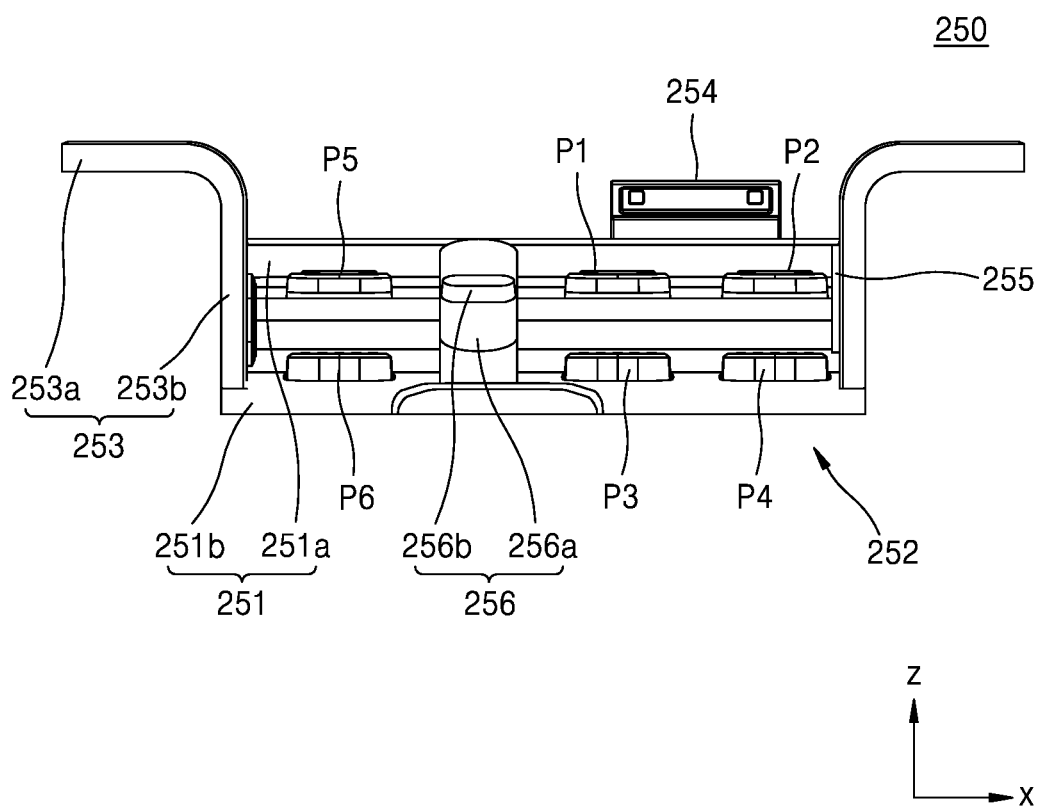

FIGS. 7 and 8 are views of a foot pedal unit 250 according to another embodiment.

Referring to FIGS. 7 and 8, the foot pedal unit 250 may include a foot panel 251 having the first step 151a and the second step 151b, a foot pedal switch 252 including a plurality of first switches 252a and a plurality of second switches 252b, footrests 253 each including a connecting wall 253b and a foot plate 253a, a first sensor 254, a second sensor 255, and a first sub-footrest 256. The foot panel 251, the foot pedal switch 252, the footrests 253, and the first sensor 254 of the foot pedal unit 250 are the same as the corresponding components of the foot pedal unit 150 according to the above-described embodiment, and thus a detailed description thereof will be omitted herein.

The first sub-footrest 256 is arranged between the footrests 253 which are on opposite sides, and protrudes upward from the foot panel 251. The first sub-footrest 256 may be used to distinguish a plurality of foot pedal switches arranged on the foot panel 251 from each other. For example, the first sub-footrest 256 may be used to distinguish the first to fourth pedal switches P1 to P4 from the fifth and sixth foot pedal switches P5 and P6.

The first sub-footrest 256 may include a first inclined surface 256a and a first recognition protrusion 256b. The first inclined surface 256a may be inclined according to a step of the foot pedal unit 250. The first recognition protrusion 256b may allow the position of the first sub-footrest 256 to be recognized by a feeling on a foot of the operator O.

The first sub-footrest 256 may be provided adjacent to any one of the footrests on opposite sides. A second sub-footrest 257 may be adjacent to any one of the footrests on opposite sides and arranged opposite the first sub-footrest 256. The operator O may rest his or her feet more comfortably using the first sub-footrest 256. For example, when the operator O temporarily stops an operation, the operator may take a break easily and comfortably by resting his or her feet on any one of the footrests 253 and the first sub-footrest 256.

Figure 9A:
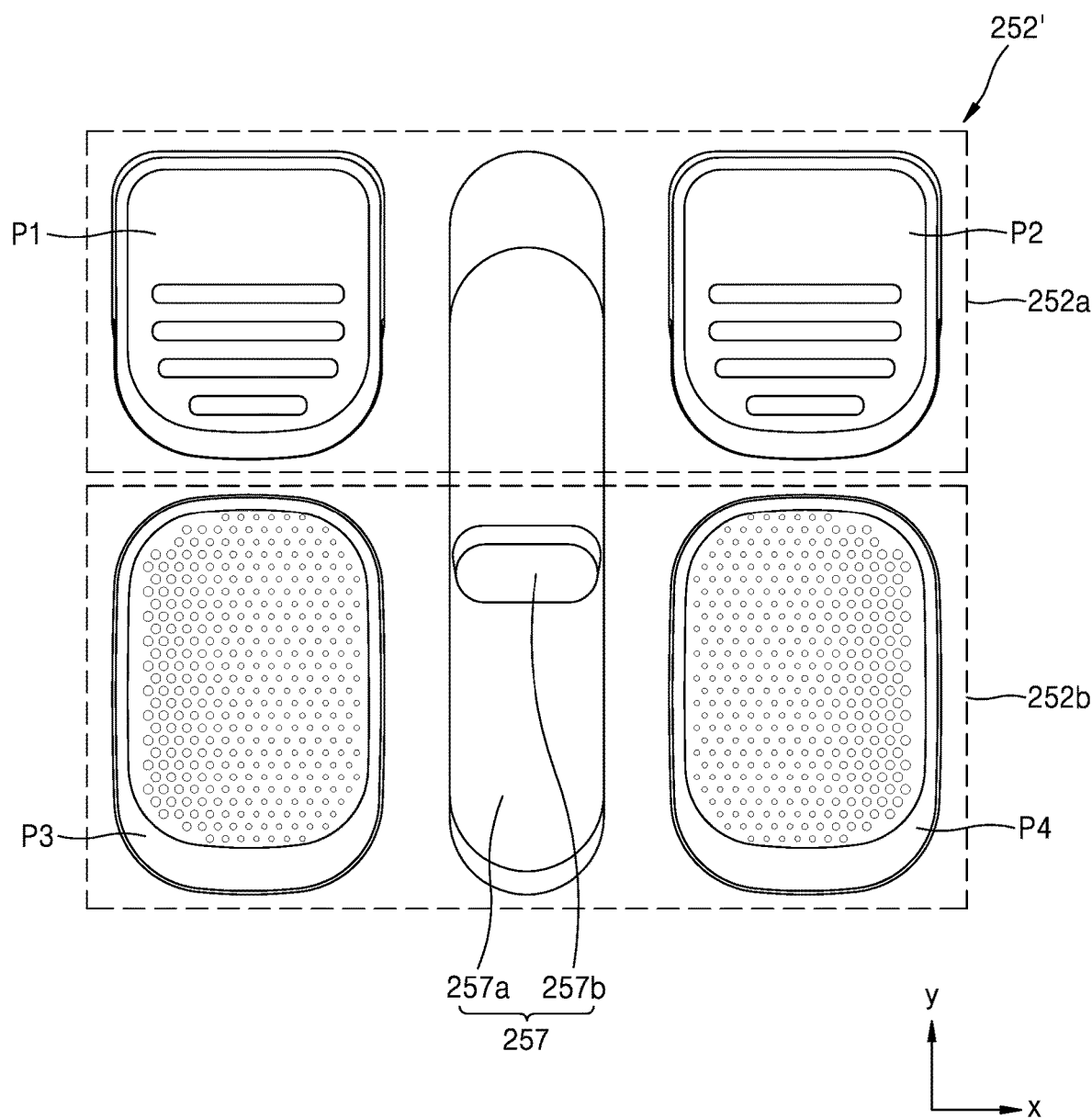
FIGS. 9A, 9B, and 9C are views illustrating foot pedal switches according to another embodiment.
Figure 9B:
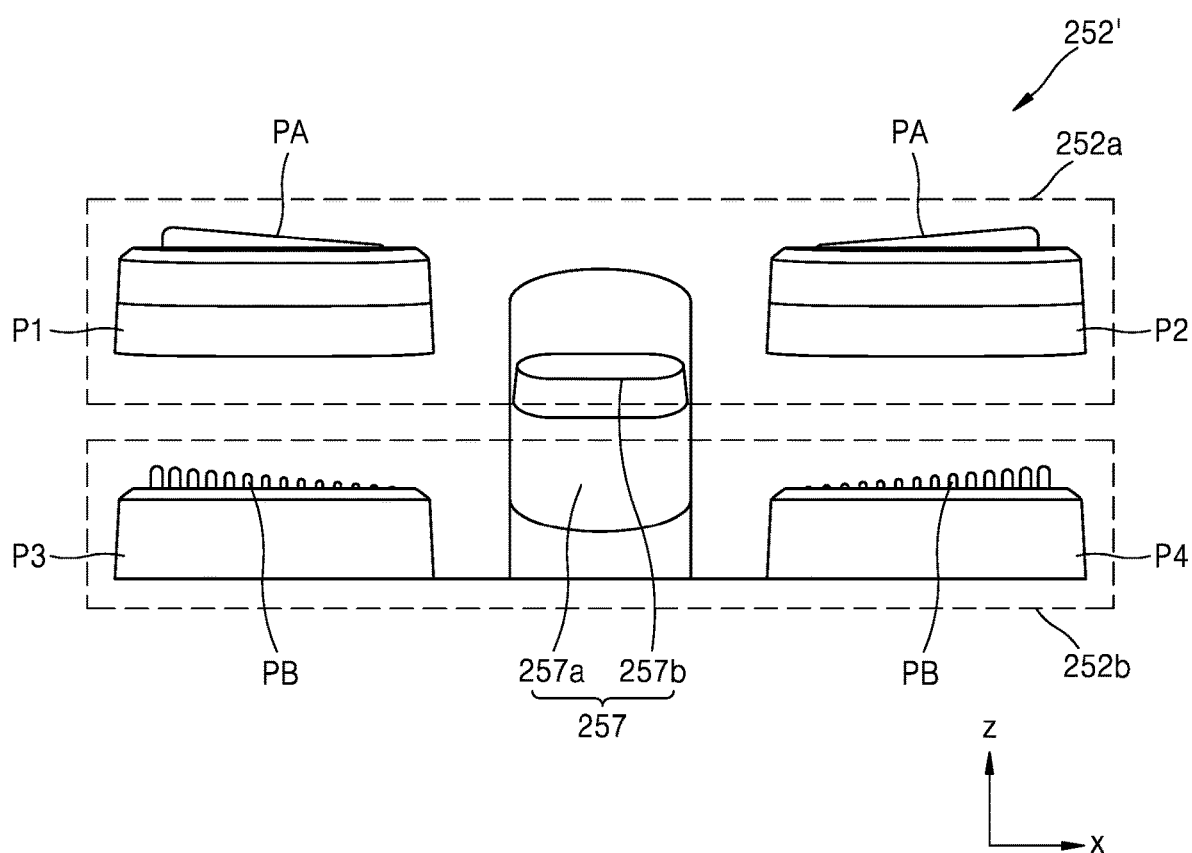
Figure 9C:
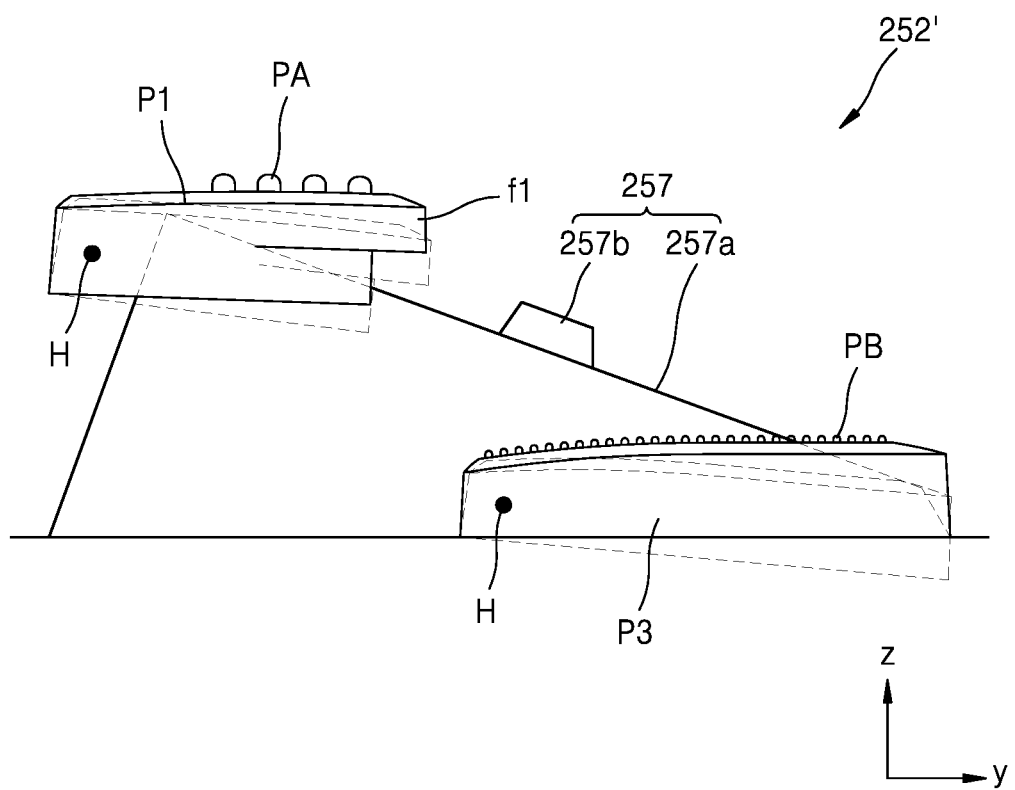

FIGS. 9A, 9B, and 9C are views illustrating a foot pedal switch 252' according to another embodiment.

Referring to FIGS. 9A, 9B, and 9C, the foot pedal switch 252' may include a plurality of first switches 252a and a plurality of second switches 252b that have different patterns, i.e., a first pattern PA and a second pattern PB, respectively. The first pattern PA and the second pattern PB are configured such that an amount by which they protrude increases in an outward direction, and thus the operator O may easily recognize a position in a left or right direction.

One or each of the first and second switches 252a and 252b of the foot pedal switch 252' has a rotational shaft H formed at a rear end thereof, and thus the operator O can press a front end f1. The first pattern PA and the second pattern PB may be provided at a front side of the switch pressed by the operator O so that shapes of the patterns can be easily recognized.

The first switches 252a include a first pedal switch P1 and a second pedal switch P2, and the second witches 552b include a third pedal switch P3 and a fourth pedal switch P4. The second sub-footrest 257 may be provided between the first pedal switch P1 and the second pedal switch P2 and between the third pedal switch P3 and the fourth pedal switch P4. That is, the second sub-footrest 257 may be provided across the first step 151a and the second step 151b in the first direction.

The second sub-footrest 257 may include a second inclined surface 257a and a second recognition protrusion 257b. The second inclined surface 257a may be inclined along the first step 151a and the second step 151b. The operator O may sense positions of the first step 151a and the second step 151b via the second recognition protrusion 257b.

The second sub-footrest 257 may be used to distinguish the first to fourth pedal switches P1 to P4 provided at the left and right sides of the foot pedal switch 252'. The operator O may distinguish the first pedal switch P1 from the second pedal switch P2 and distinguish the third pedal switch P3 from the fourth pedal switch P4, by using the second sub-footrest 257. In addition, the second sub-footrest 257 may be used to distinguish the first and second pedal switches 252a and 252b provided in a height direction of the foot pedal switch 252' from each other. In other words, the operator O may recognize relative positions of the first switches 252a and the second switches 252b by recognizing the second recognition protrusion 257b.

The operator O may rest his or her feet more comfortably by using the second sub-footrest 257. For example, when the operator O temporarily stops an operation, the operator may easily and comfortably take a break by resting his or her feet on any one of the footrests 153 and the second sub-footrest 257.

Figure 10A:
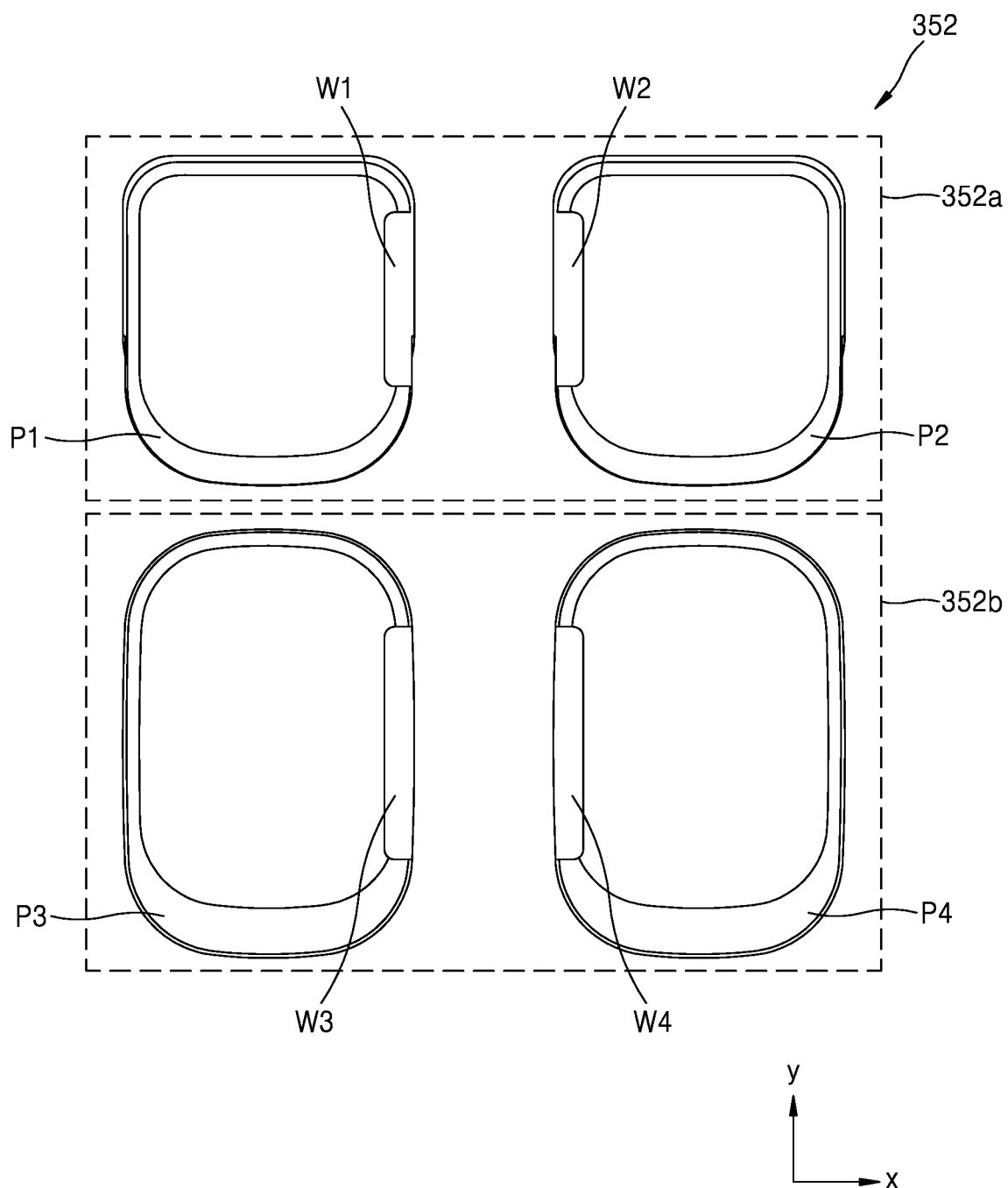
FIGS. 10A and 10B are views illustrating foot pedal switches according to another embodiment.
Figure 10B:
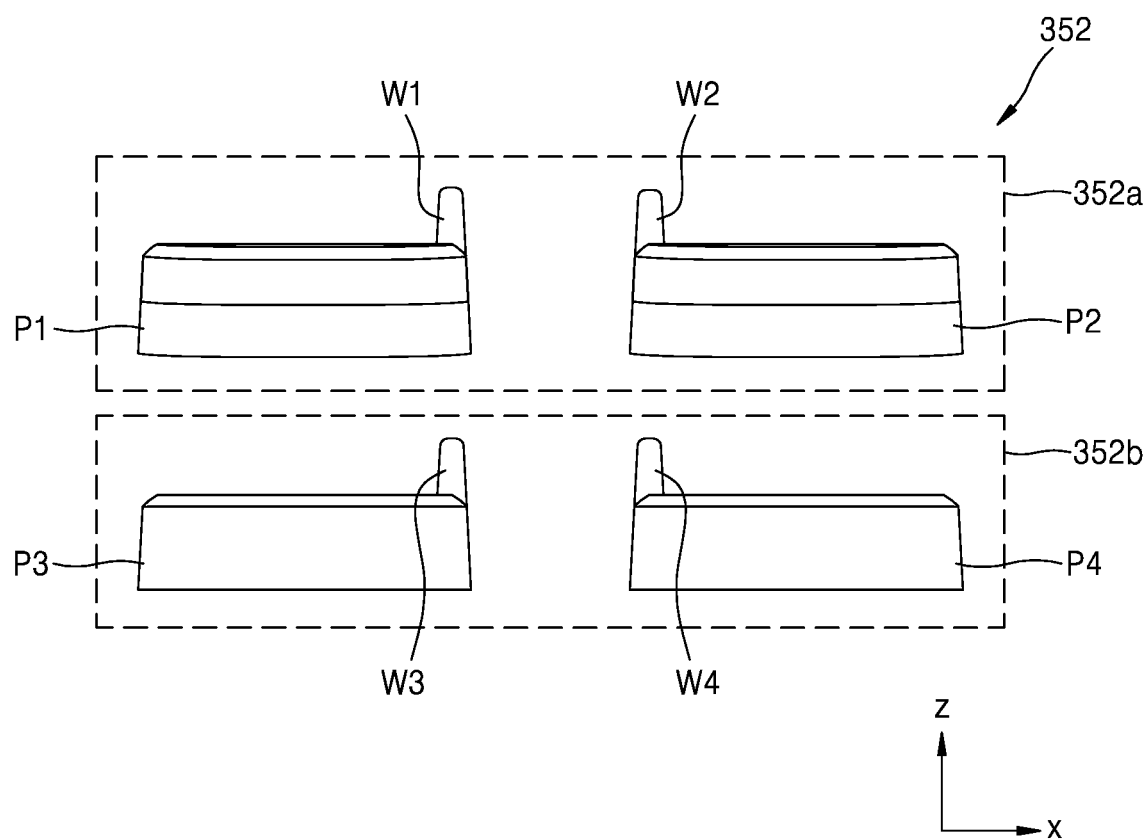

FIGS. 10A and 10B are views illustrating a foot pedal switch 352 according to another embodiment.

Referring to FIGS. 10A and 10B, the foot pedal switch 352 may include a plurality of first switches 352a, a plurality of second switches 352b, and protrusions. The first switches 352a include a first pedal switch P1 and a second pedal switch P2, and the second switches 352b include a third pedal switch P3 and a fourth pedal switch P4.

The first switches 352a are provided on the first step 151a and each of the first switches 352a has a first protrusion protruding from an opposite side surface to that of the other, and the second switches 352b are provided on the second step 151b and each of the second switches 352b has a second protrusion protruding from an opposite side surface to that of the other. The first protrusions and the second protrusions may be aligned in parallel in the first direction (y axis).

In detail, a first wall W1 protrudes in a projection form from a right side of the first pedal switch P1, and a second wall W2 protrudes in a projection form from a left side of the second pedal switch P2. A third wall W3 protrudes in a projection form from a right side of the third pedal switch P3, and a fourth wall W4 protrudes in a projection form from a left side of the fourth pedal switch P4 as shown in FIG. 10B.

The operator O may distinguish the first pedal switch P1 from the second pedal switch P2 by sensing positions of the first wall W1 and the second wall W2, and may distinguish the third pedal switch P3 from the fourth pedal switch P4 by sensing positions of the third wall W3 and the fourth wall W4.

Figure 11A:
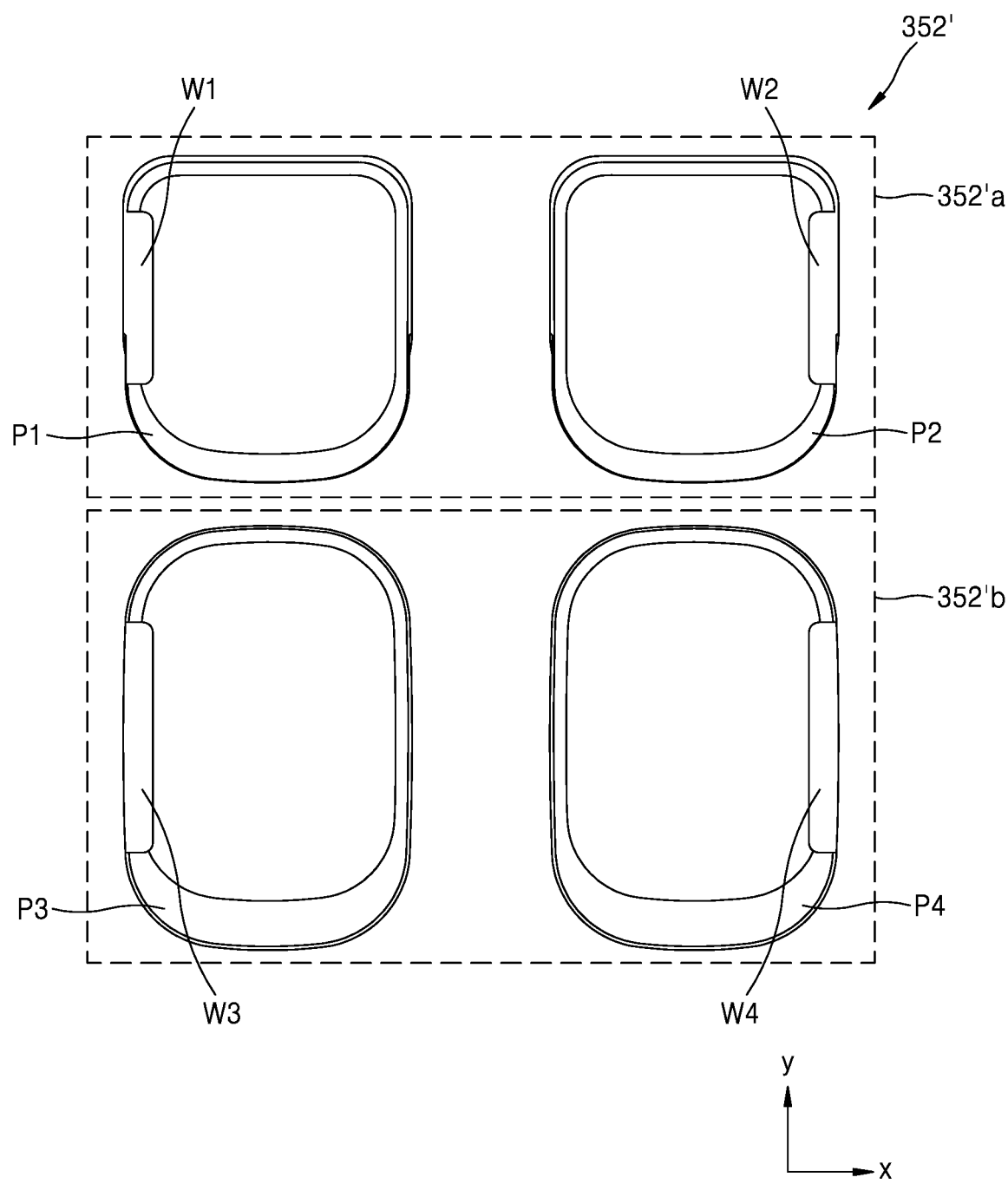
FIGS. 11A and 11B are views illustrating foot pedal switches according to another embodiment.
Figure 11B:
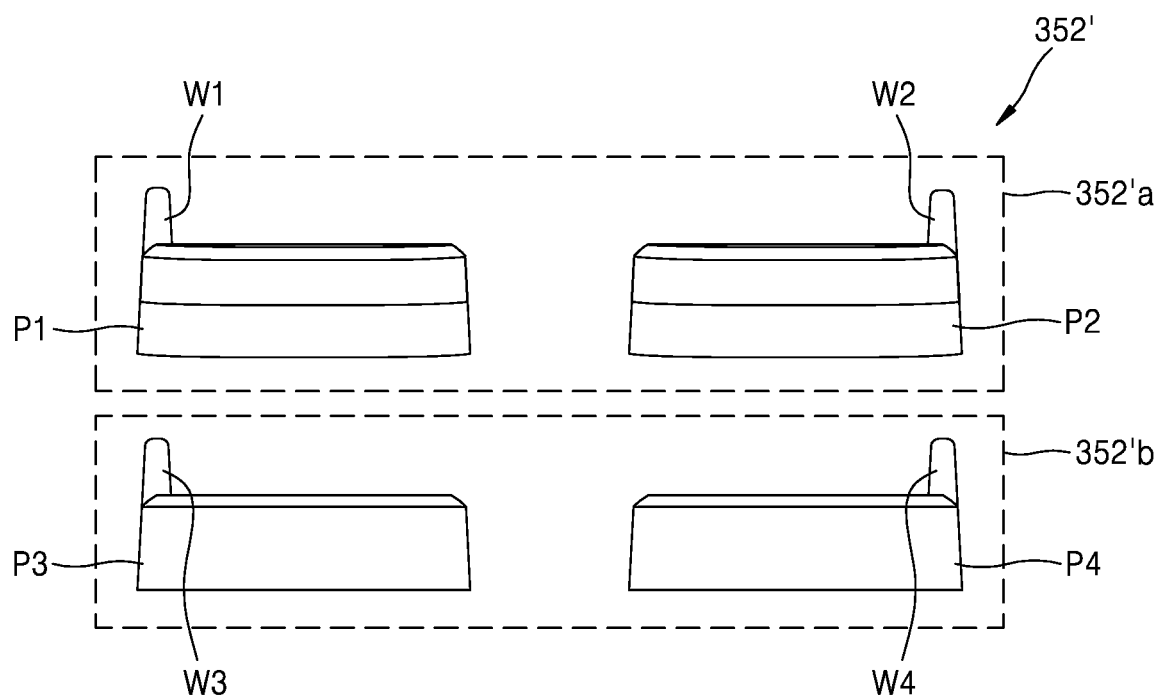

FIGS. 11A and 11B are views illustrating a foot pedal switch 352' according to another embodiment.

Referring to FIGS. 11A and 11B, projections of the foot pedal switch 352' protrude in a direction opposite to that illustrated in FIG. 10A. That is, the first wall W1 protrudes in a projection form from a left side of the first pedal switch P1, and the second wall W2 protrudes in a projection form from a right side of the second pedal switch P2. The third wall W3 protrudes in a projection form from a left side of the third pedal switch P3, and the fourth wall W4 protrudes in a projection form from a right side of the fourth pedal switch P4.

The operator O may distinguish the first pedal switch P1 from the second pedal switch P2 by sensing positions of the first wall W1 and the second wall W2, and may distinguish the third pedal switch P3 from the fourth pedal switch P4 by sensing positions of the third wall W3 and the fourth wall W.

Figure 12A:
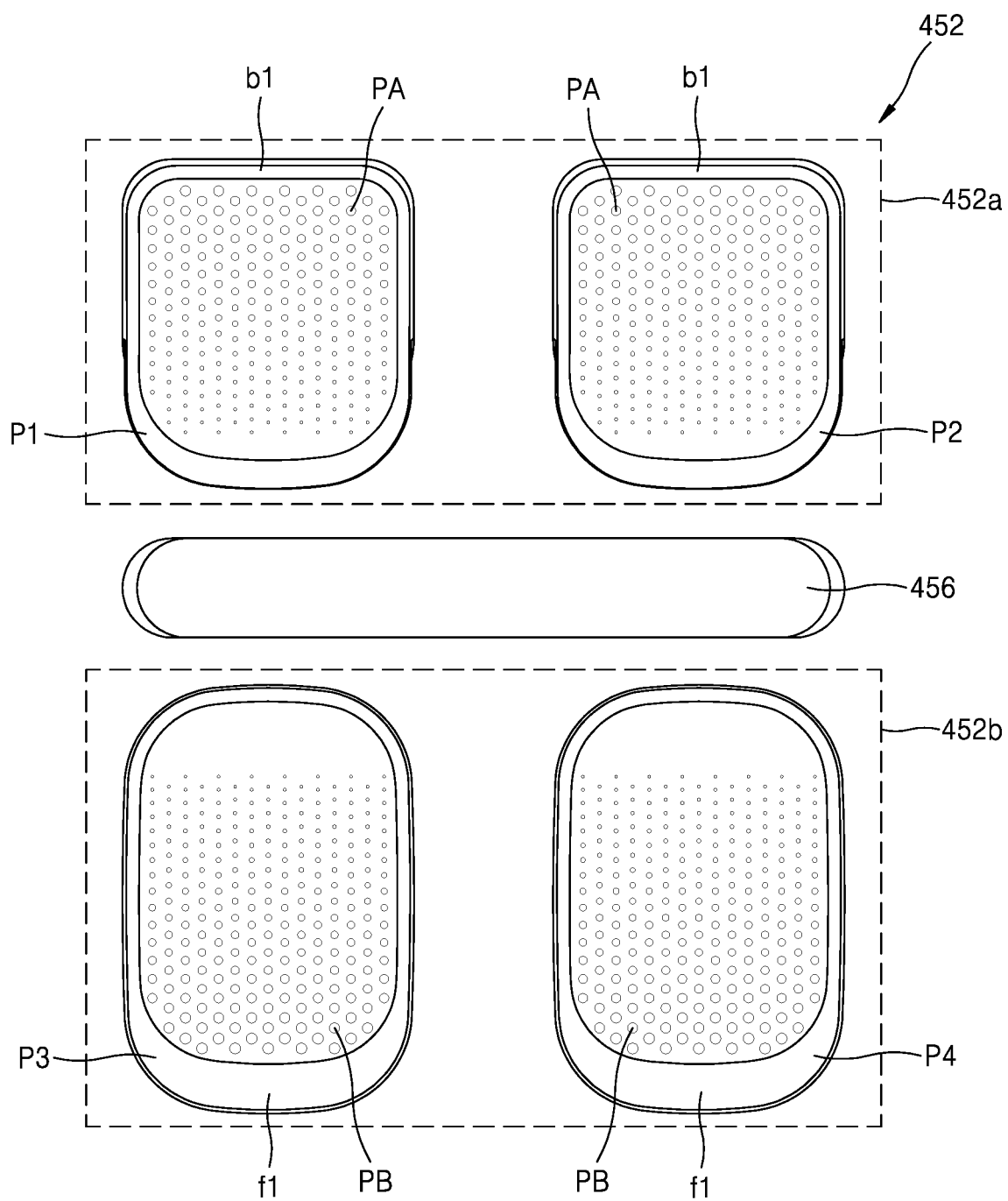
FIGS. 12A, 12B, and 12C are views illustrating foot pedal switches according to another embodiment.
Figure 12B:
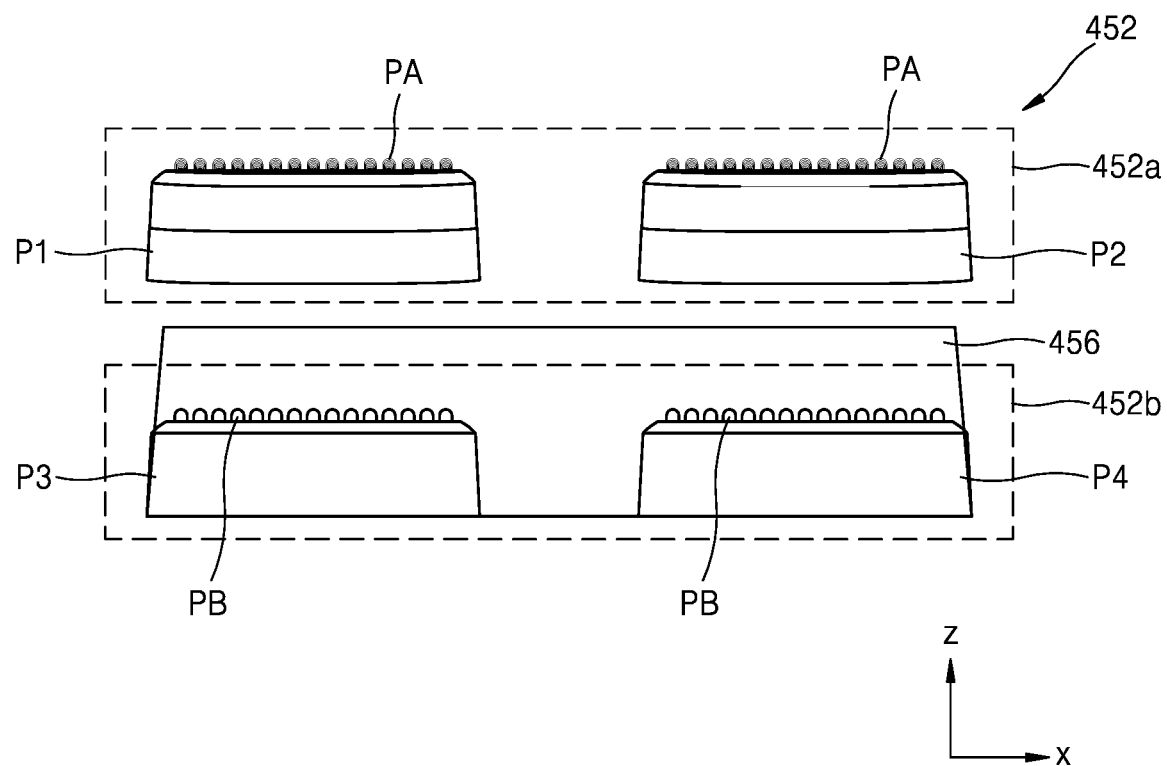
Figure 12C:
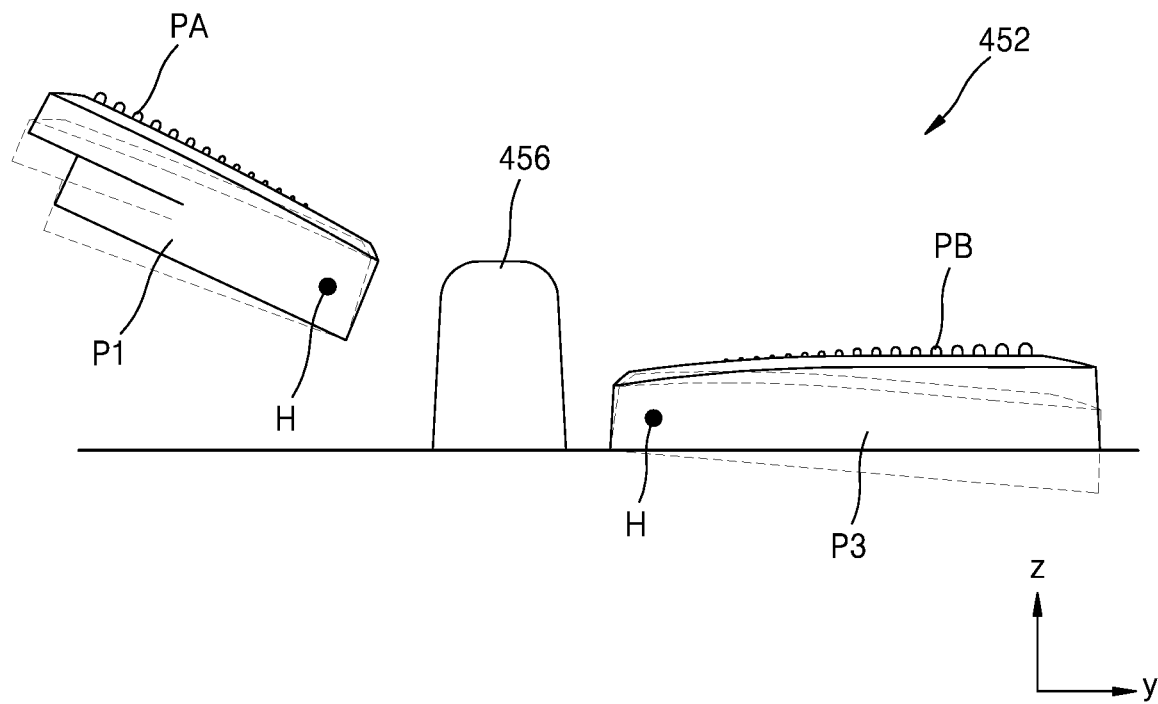

FIGS. 12A, 12B, and 12C are views illustrating a foot pedal switch 452 according to another embodiment.

Referring to FIGS. 12A, 12B, and 12C, the foot pedal switch 452 may include a plurality of first switches 452a inclined with respect to a surface of the first step 151a and having a first pattern PA on outer sides thereof, and a plurality of second switches 452b provided flat on a surface of the second step 151b and having a second pattern PB different from the first pattern PA.

The first switches 452a each have a rotational shaft H provided at a front end portion thereof such that the first switches 452a can be operated by a foot of the operator O pressing a rear end portion b1. An amount by which the first pattern PA protrudes may increase towards the rear end portion b1 so that the operator O easily senses the first pattern PA. The second switches 452b each have a rotational shaft H provided at a rear end portion thereof such that the second switches 452b can be operated by a foot of the operator O pressing a front end portion f1. An amount by which the second pattern PB protrudes may increase towards the front end portion f1 so that the operator O can easily sense the second pattern PB.

In other embodiments, the diameter of the first pattern PA of the first switches 452a may increase towards the rear end portion b1, and the diameter of the second pattern PB of the second switches 452b may decrease towards the front end portion f1.

Since a position where each of the first switches 452a is pressed is a rear end, and a position where each of the second switches 452b is pressed is a front end, the operator O may distinguish the first switches 452a from the second switches 452b by distinguishing the pressing positions from each other. In addition, since protruding directions or amounts of the first switches 452a and the second switches 452b are opposite to each other, the operator O may distinguish the first switches 452a from the second switches 452b by distinguishing the protruding directions or amounts from each other.

The operator O may easily distinguish the first switches 452a from the second switches 452b due to a difference in their respective inclination angles. In addition, since the first switches 452a are inclined, a rear end of each of the first switches 452a may be pressed in a state in which the foot of the operator O is rested thereon.

A third sub-footrest 456 may be provided between the first step 151a and the second step 151b. The third sub-footrest 456 may extend in the second direction (x axis) so that the first switches 452a may be distinguished from the second switches 452b.

The third sub-footrest 456 may provide the operator O with a cushioning sense, and thus the operator O may comfortably press the first switches 452a. That is, the rear portion of a foot of the operator O may be supported by the third sub-footrest 456, and thus the foot pedal switch 452 may be comfortably manipulated.

The operator O may rest his or her feet more comfortably using the third sub-footrest 456. For example, when the operator O temporarily stops an operation, the operator O may take a break easily and comfortably by resting his or her foot on the third sub-footrest 456.

Figure 13A:
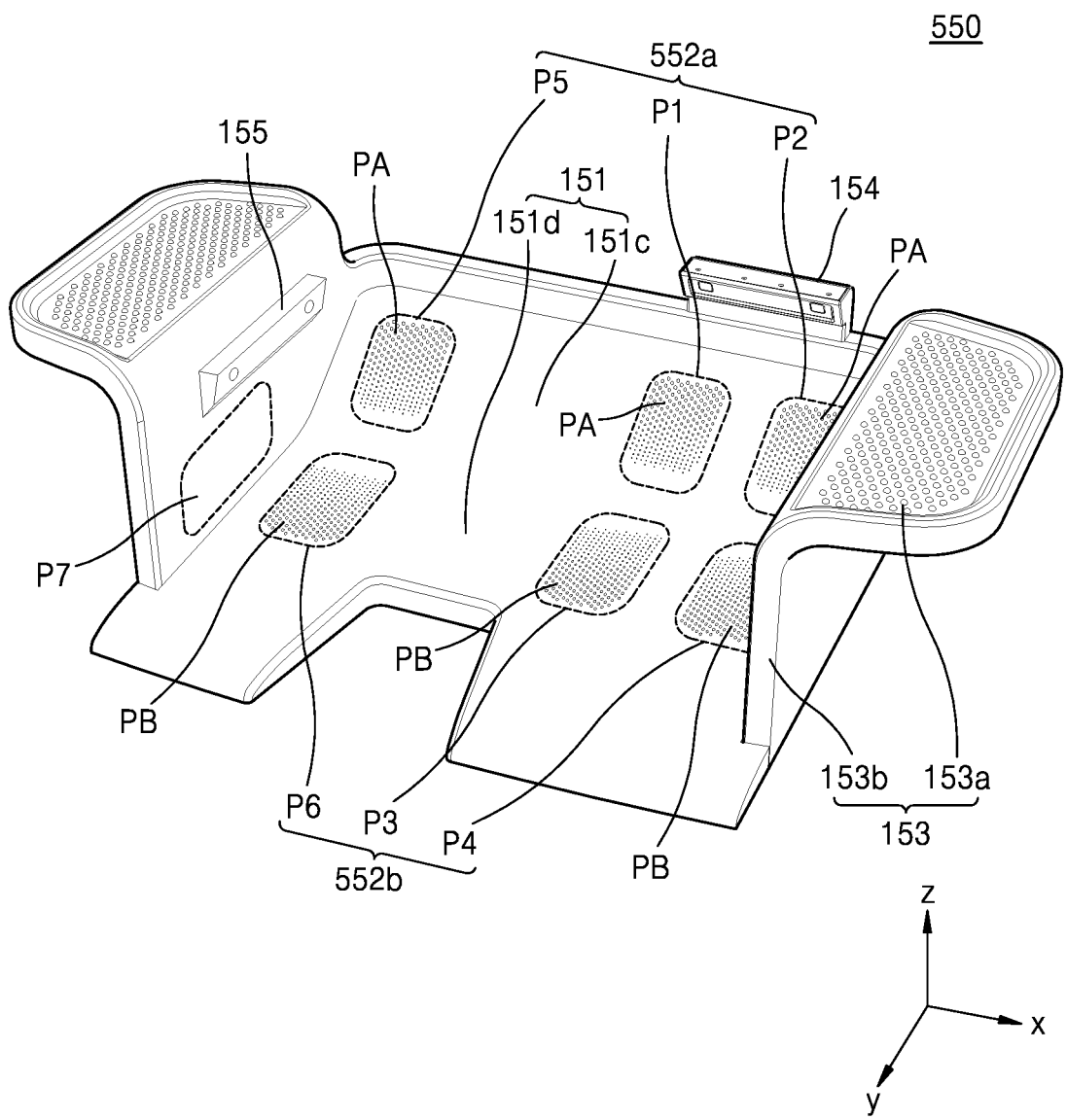
FIGS. 13A and 13B are views illustrating a foot pedal unit according to another embodiment.
Figure 13B:
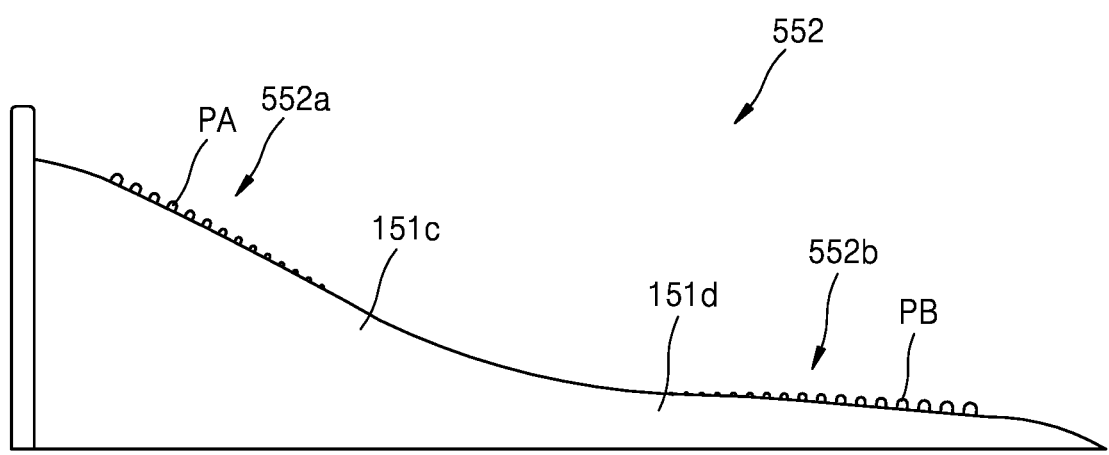

FIGS. 13A and 13B are views illustrating a foot pedal unit 550 according to another embodiment.

Referring to FIGS. 13A and 13B, in the foot pedal unit 550 according to another embodiment, a foot pedal switch 552 may be configured with a touch sensor that senses a touch of the operator O, and generates a signal corresponding thereto. In other words, the foot pedal unit 550 according to another embodiment may be used to manipulate an input instrument by sensing a touch of the operator O, without including a mechanical switch in which a modification occurs due to operation of the operator O. In this regard, the operator O may recognize the position and function of a switch of each of a plurality of pedals via the first pattern PA or the second pattern PB formed on an outer surface of the touch sensor.

In particular, the foot pedal unit 550 may include a first surface 151c having a first slope with respect to the ground and a second surface 151d extending from the first surface 151c and having a second slope different from the first slope. As illustrated in the drawings, the first slope of the first surface 151c may be greater than that of the second surface 151d. Due to such a slope difference, the operator O may distinguish a first switch 552a from a second switch 552b without a step of the foot pedal unit 550.

The foot pedal switch 552 may include a plurality of first switches 552a each including a first touch sensor provided on the first surface 151c and having the first pattern PA on an outer surface of the first touch sensor, and a plurality of second switches 552b each including a second touch sensor provided on the second surface 151d and having the second pattern PB different from the first pattern PA on an outer surface of the second touch sensor. In this regard, the first touch sensor and the second touch sensor may be pressurizing-type touch sensors that sense a touch by pressure. However, the technical spirit of the present disclosure is not limited thereto, and a capacitive touch sensor may also be used.

The first pattern PA and the second pattern PB may be provided at positions pressed by the foot of the operator O. The operator O may manipulate input instructions using the foot pedal switch 552, with low pressure such as a touch, unlike a switch that senses an input instruction by mechanical modification. An amount by which at least one of the first pattern PA and the second pattern PB protrudes may gradually increase in a direction.

Meanwhile, the first touch sensors of the first switches 552a and the second touch sensors of the second switches 552b may be formed integrally with the first surface 151c and the second surface 151d, respectively, or may be arranged on the same plane. When a touch of the operator O is sensed, the first touch sensor or the second touch sensor generates an operation signal, and the controller 40 may be connected to each pedal switch and receive the operation signal from the corresponding pedal switch to drive the slave robot 10.

In addition, when the operation signal is received, the controller 40 may control a speaker (not shown) configured to provide the operator O with a voice signal or a vibration motor (not shown) configured to provide the operator O with a vibration signal to be driven and provide a feedback for the touch, thereby enhancing recognition of the operator O. At this time, although not shown in the drawings, the vibration motor (not shown) may be provided adjacent to the first switches 552a or the second switches 552b, and the operator O may recognize the positions of pedal switches via different vibrations according to manipulation of each pedal switch.

The foot pedal switch 552 may minimize mechanical gap exposure and have a simple shape, thereby enhancing a hygienic environment of medical equipment. In particular, a protruding-type mechanical pedal is not needed, and thus the feet of the operator O may be naturally rested on a plane, and accordingly, fatigue of the operator O may be minimized.

Figure 14:
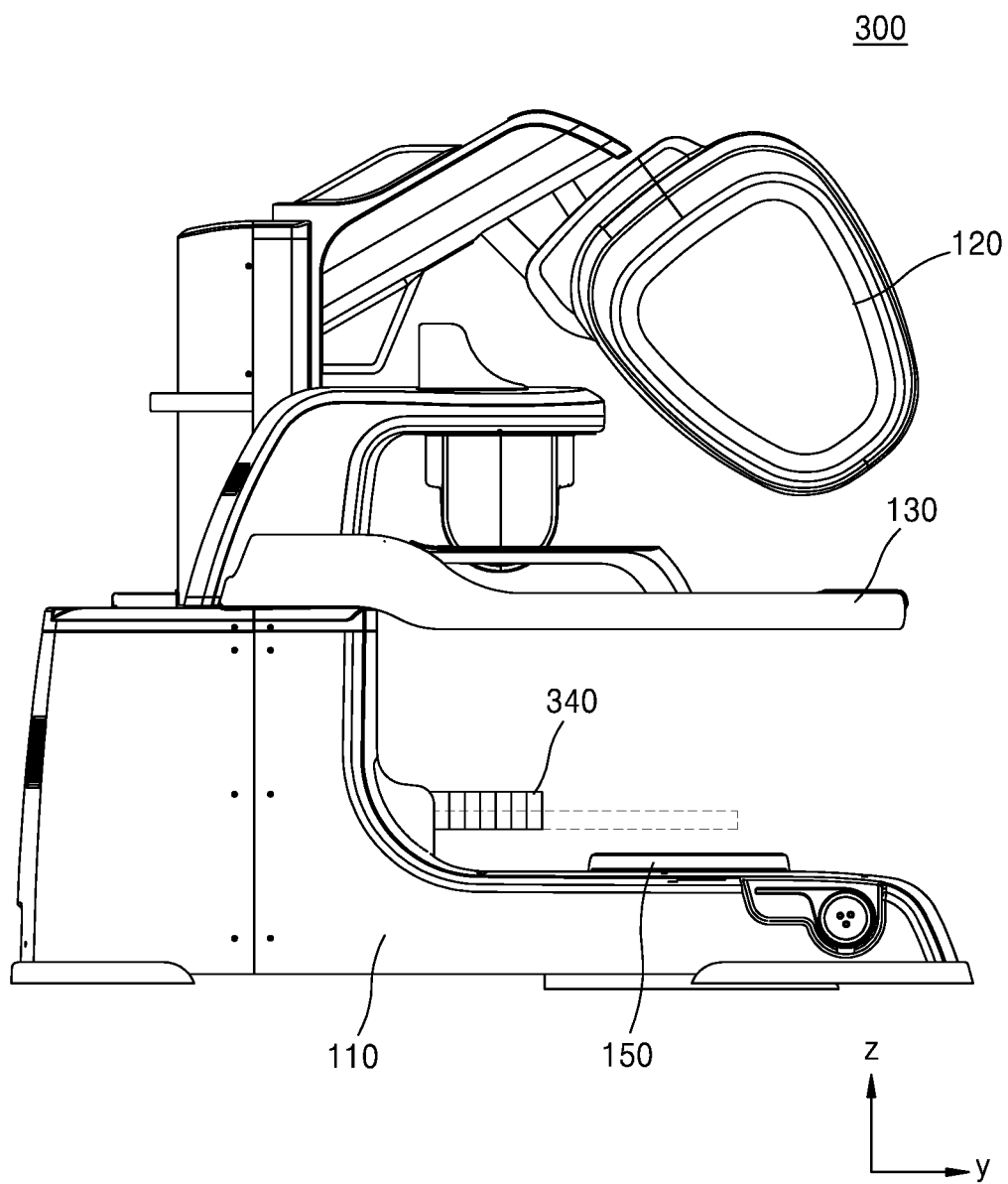
FIG. 14 is a side view illustrating a master console for a surgical robot according to another embodiment.

FIG. 14 is a perspective view of a master console 300 for a surgical robot, according to another embodiment.

Referring to FIG. 14, the master console 300 may include a base unit 110, a head unit 120, a manipulation unit 130, a foot pedal unit 150, and a footrest 340.

The footrest 340 may be provided on a side of the base unit 110, and may be unfolded over the foot pedal unit 150 through manipulation by the operator O. For example, when the operator O presses a side of the footrest 340, the folded footrest 340 may be unfolded such that it is located above the foot pedal unit 150. The footrest 340 is activated to cover foot pedal switches, and thus pressing of the foot pedal switches by mistake of the operator O may be prevented.

As is apparent from the foregoing description, an operator who manipulates the master console can comfortably and easily rest his or her feet on footrests, and thus fatigue of the operator can be reduced, and the master console with enhanced convenience and enhanced safety may be provided.

In addition, an operator who manipulates the master console can easily and accurately recognize each of a plurality of foot pedal switches, and thus the master console for a surgical robot which exhibits enhanced manipulation and enhanced safety may be provided.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A master console for a surgical robot, the master console comprising:
    a base including a first base and a second base, the first and second bases being disposed parallel to each other; and
    a foot pedal arranged between the first base and the second base,
    wherein the foot pedal comprises:
        at least one foot pedal switch configured to be manipulated by a foot of an operator;
        a foot panel configured to support the at least one foot pedal switch; and
        a footrest extending outward from the foot panel, and
    wherein the footrest is inclined with respect to an upper surface of the base.

2. The master console of claim 1, wherein the foot pedal is configured to move along the first base and the second base according to body information of the operator.

3. The master console of claim 1, wherein the footrest extends such that the footrest surrounds at least one of the first base and the second base.

4. The master console of claim 1, wherein the foot pedal further comprises a sub-footrest protruding from an upper surface of the foot panel and located between the first base and the second base.

5. The master console of claim 4, wherein the sub-footrest comprises:
    an inclined surface inclined with respect to a ground; and
    a recognition protrusion protruding from the inclined surface.

6. The master console of claim 1, wherein the at least one foot pedal switch comprises:
    a pair of first switches disposed on a surface of the foot panel, and each having a first protrusion protruding from a side of each of the pair of first switches, the sides having the first protrusions being disposed opposite to each other; and
    a pair of second switches disposed on another surface of the foot panel at a height different from that of the pair of first switches, and each having a second protrusion protruding from a side of each of the pair of second switches, the sides having the second protrusions being disposed opposite to each other.

7. A master console for a surgical robot, the master console comprising:
    a base including a first base and a second base, the first and second bases being disposed parallel to each other; and
    a foot pedal arranged between the first base and the second base,
    wherein the foot pedal comprises:
        at least one foot pedal switch configured to be manipulated by a foot of an operator;
        a foot panel configured to support the at least one foot pedal switch; and
        a footrest extending outward from the foot panel,
    wherein the at least one foot pedal switch comprises:
        at least one first switch disposed on a surface of the foot panel, wherein a first pattern is defined on an outer surface of the at least one first switch; and
        at least one second switch disposed on another surface of the foot panel at a height different from that of the at least one first switch, wherein a second pattern is defined on an outer surface of the at least one second switch, the second pattern being different from the first pattern.

8. The master console of claim 7, wherein an amount by which at least one of the first pattern and the second pattern protrudes gradually increases in a direction.

9. The master console of claim 7, wherein the foot pedal further comprises:
    a first sensor configured to sense a position of the foot of the operator in a leftward or rightward direction; and
    a second sensor configured to sense the position of the foot of the operator in a forward or backward direction.

10. The master console of claim 7, wherein the at least one first switch is inclined with respect to the foot panel, and the at least one second switch is parallel to the foot panel.

11. The master console of claim 10, wherein a rotational shaft is disposed in a front end portion of the at least one first switch such that the at least one first switch is operable by the foot of the operator pressing a rear end portion of the at least one first switch, and another rotational shaft is disposed in a rear end portion of the at least one second switch such that the at least one second switch is operable by the foot of the operator pressing a front end portion of the at least one second switch.

12. The master console of claim 10, wherein the at least one first switch is configured such that an amount by which the first pattern protrudes increases towards a rear end portion of the at least one first switch, and the at least one second switch is configured such that an amount by which the second pattern protrudes increases towards a front end portion of the at least one second switch.

13. The master console of claim 7, wherein the foot panel comprises a first step and a second step,
    wherein the at least one first switch includes a first pedal switch and a second pedal switch disposed on the first step, and
    wherein the at least one second switch includes a third pedal switch and a fourth pedal switch disposed on the second step.

14. The master console of claim 13, wherein a height of the second pattern of the third pedal switch gradually increases in a direction and a height of the second pattern of the fourth pedal switch gradually increases in another direction opposite to the direction of the pattern of the third pedal switch.

15. The master console of claim 13, wherein the at least one first switch further includes a fifth pedal switch disposed on the first step and the at least one second switch further includes a sixth pedal switch disposed on the second step, and wherein the foot pedal further comprises a sub-footrest located on the first and second steps and between the first pedal switch and the fifth pedal switch, such that the sub-footrest is configured to distinguish locations of the first to fourth pedal switches from those of the fifth and sixth pedal switches.

16. The mater console of claim 15, wherein the foot pedal further comprises a seventh pedal switch disposed on a side surface thereof.

17. The master console of claim 13, wherein the foot pedal further comprises a sub-footrest located on the first and second steps and between the first pedal switch and the second pedal switch, such that the sub-footrest is configured to distinguish locations of the first and third pedal switches from those of the second and fourth pedal switches.

18. A master console for a surgical robot, the master console comprising:
- a base including a first base and a second base, the first and second bases being disposed parallel to each other; and
- a foot pedal arranged between the first base and the second base, wherein the foot pedal comprises:
- at least one foot pedal switch configured to be manipulated by a foot of an operator;
- a foot panel configured to support the at least one foot pedal switch; and
- a footrest extending outward from the foot panel, wherein the foot panel comprises a first surface and a second surface, the first surface having a first slope with respect to a ground and the second surface having a second slope different from that of the first surface, and is located between the first base and the second base, and wherein the at least one foot pedal switch comprises:
- at least one first switch including a first touch sensor disposed on the first surface; and
- at least one second switch including a second touch sensor disposed on the second surface.

19. The master console of claim 18, wherein a first pattern is defined on an outer surface of the first touch sensor and a second patter is defined on an outer surface of the second touch sensor, the first and second patterns being different from each other.

* * * * *